United States Patent [19]

Schneider

[11] Patent Number: 4,465,077

[45] Date of Patent: Aug. 14, 1984

[54] APPARATUS AND METHOD OF DETERMINING FERTILITY STATUS

[76] Inventor: Howard Schneider, 149 Finchley Rd., Montreal, Quebec, Canada, H3X 3A3

[21] Appl. No.: 320,227

[22] Filed: Nov. 12, 1981

[51] Int. Cl.³ ............................................. A61B 5/00
[52] U.S. Cl. .................................. 128/738; 128/736; 364/417
[58] Field of Search ................ 128/736, 738; 364/413, 364/415, 417

[56] References Cited

U.S. PATENT DOCUMENTS

| | | | |
|---|---|---|---|
| 3,406,015 | 10/1968 | Foster | 23/230 |
| 3,675,640 | 7/1972 | Gatls | 128/671 |
| 3,749,089 | 7/1973 | Derr | 128/2.1 E |
| 3,924,609 | 12/1975 | Friedenberg et al. | 128/2.1 |
| 3,926,037 | 12/1975 | Kopito et al. | 73/53 |
| 3,982,423 | 9/1976 | Schuster | 73/54 |
| 3,986,494 | 10/1976 | Preti et al. | 128/2 R |
| 4,010,738 | 3/1977 | Preti et al. | 128/2 R |
| 4,013,066 | 3/1977 | Schuster | 128/2 R |
| 4,031,365 | 6/1977 | Guglielmo et al. | 235/151.3 |
| 4,036,212 | 7/1977 | Karuhn | 128/2 R |
| 4,101,962 | 7/1978 | Hokato | 364/413 |
| 4,119,089 | 10/1978 | Preti et al. | 128/2 R |
| 4,148,304 | 4/1979 | Mull | 128/2 R |
| 4,151,831 | 5/1979 | Lester | 128/736 |
| 4,151,833 | 5/1979 | Polishuk | 128/738 |
| 4,184,202 | 1/1980 | McCrae | 364/413 |
| 4,246,907 | 1/1981 | Bullock | 128/738 |
| 4,367,527 | 1/1983 | Desjacques | 128/738 |

FOREIGN PATENT DOCUMENTS

| | | | |
|---|---|---|---|
| 2803152 | 7/1979 | Fed. Rep. of Germany | 128/738 |
| 2847397 | 5/1980 | Fed. Rep. of Germany | 128/738 |

OTHER PUBLICATIONS

"An 8-Digit Calculator that Charts Biorythm", Casio Corporation, Japan (undated).
"A Year's Experience with a Fertility Awareness Program: A Report" by Rogow et al., Advances in Planned Parenthood 1980; 15:27–33.
"A Randomized Prospective Study of the Use-Effectiveness of Two Methods of Natural Family Planning: An Interim Report" by Wade et al. (Am. J. Obstet. Gynecol. 134-628, 1979).
"Optimal Features of Basal Body Temperature Recordings Associated with Conceptional Cycles" by Matthews et al., Int. J. Fertil. 24(4), 1980, pp. 318–320.
"Symptoms and Hromonal Changes Accompanying Ovulation" by Billings et al., The Lancet, Feb. 5, 1972.
"Detection of Ovulation by the Basal Body Temperature Method" by Gerhard K. Döring, The Human Life Foundation, 1973.
"A Trial of the Ovulation Method of Family Planning in Tonga" by Weissman, Sister M. Cosmas, The Lancet Oct. 14, 1972.
"Cervical Mucus-Basal Body-Temperature Method of Regulating Births" by John Marshall, The Lancet, Aug. 7, 1976.
"You and Contraceptives", Parents, Jul. 1981.
Planning Your Family the S-T Way" by Parenteau-Carreau et al., 1975, pub. Serena.
"The Adjustment of Basal Body Temperature Measurements to Allow Time of Waking" by Royston et al., British Journal of Obstetrics and Gynaecology—Dec. 80, vol. 87, pp. 1123–1127.

Primary Examiner—Kyle L. Howell
Assistant Examiner—Francis J. Jaworski
Attorney, Agent, or Firm—Hamilton, Brook, Smith & Reynolds

[57] ABSTRACT

A fertility computer is disclosed having the ability to store information about a users past menstrual cycle history, basal body temperature, gynecological disorders, which along with certain prediction indicators is used to statistically predict when ovulation will occur. The prediction indicators are based on information concerning the current status of certain body indicators such as mucus change, spotting in the middle of a cycle or a sore throat. This information is processed in accordance with a predetermined program which ascribes certain values to the above parameters to predict the present fertility status of the user.

14 Claims, 19 Drawing Figures

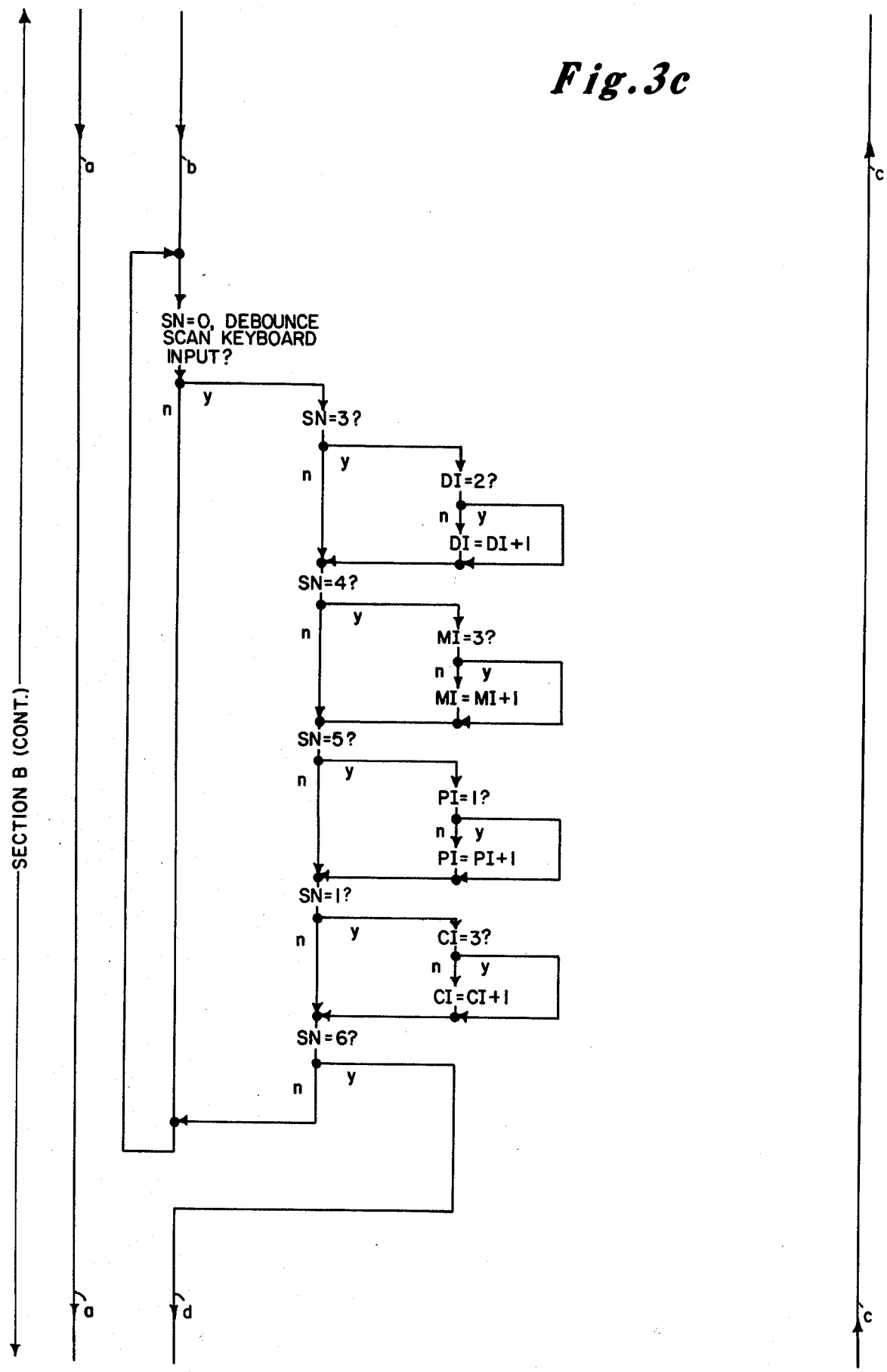

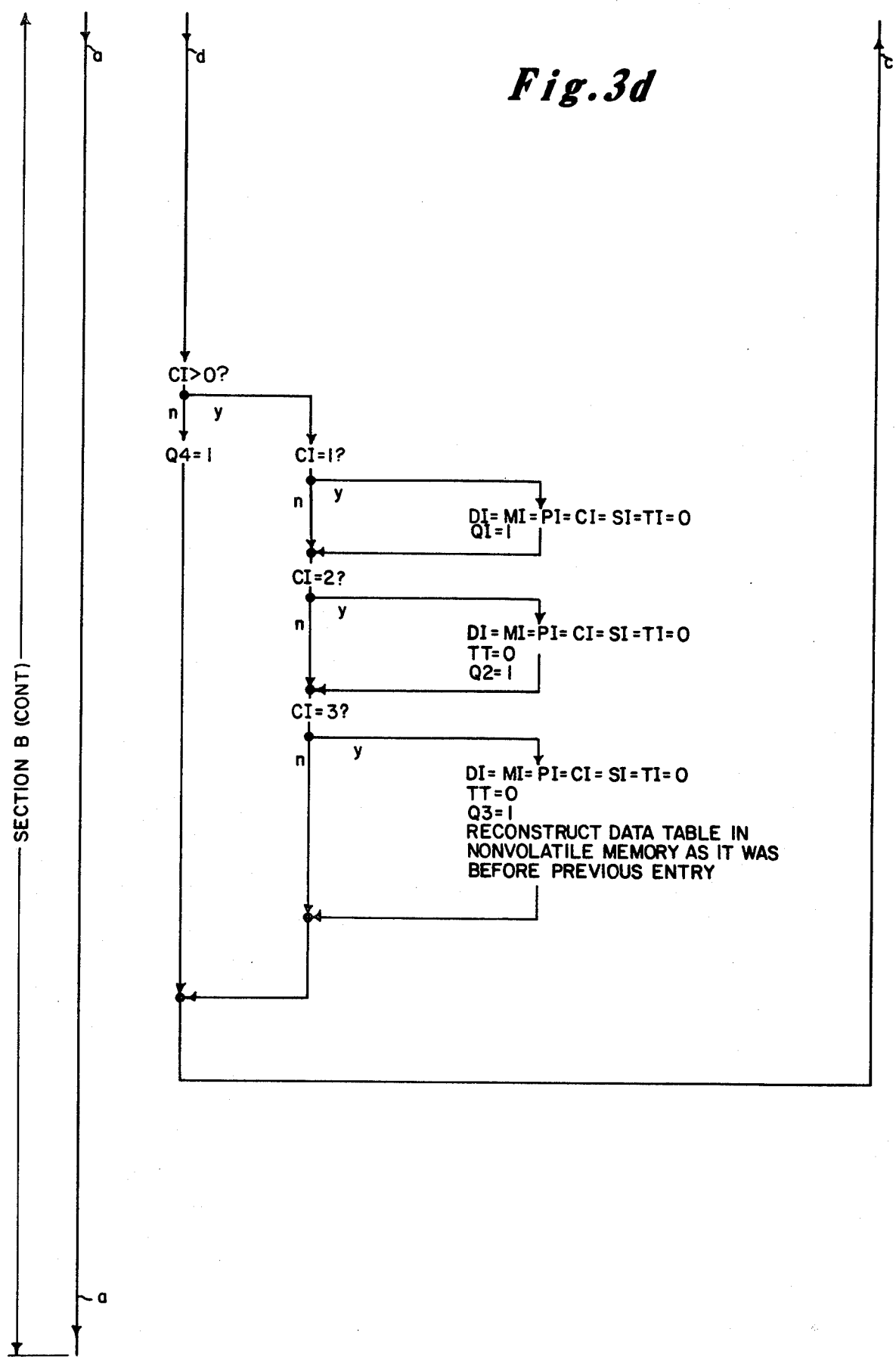

APPARATUS AND METHOD OF DETERMINING FERTILITY STATUS

DESCRIPTION

1. Technical Field

This invention is in the field of prediction, detection and diagnosis of ovulation in female mammals and more particularly human females.

2. Background Art

Ovulation prediction is important both from the viewpoint of birth control and enhancing fertility. Although much research has been done in the area of birth control and enhancing fertility, very few safe, easy to use and reliable methods or procedures, free of side effects, have resulted to date.

In respect to enhancing fertility, presently, a woman classified as infertile who wishes to become pregnant has two main alternatives. She can take fertility drugs which have significant undesirable side effects or she can attempt to predict her time of ovulation. One method of detecting and timing ovulation is the recording of waking temperature at basal conditions, i.e., basal body temperature. A rise in temperature indicates that ovulation has occurred, thereby signifying that this is the time that sexual intercourse may result in a conception.

As indicated in U.S. Pat. No. 4,151,831, one problem with basal body temperature measurement as an indicia for fertility status for a person desiring to become pregnant is that the indication does not occur until the peak time of fertility is almost over. This is because a rise in basal body temperature is indicative of a rise in serum progesterone levels which is in turn indicative of ovulation. Unfortunately, the rise in body basal temperature may not occur for a day or two after ovulation has occurred.

Some researchers believe that the unfertilized egg may not survive longer than 12 hours. Since sperm are thought to be viable up to 72 hours in the female genital tract, it definitely would be advantageous to know several days ahead of time when ovulation will occur.

In respect to the opposite case, birth control, U.S. Pat. No. 4,010,738 contains an excellent summary of the problem, as follows:

"For birth control purposes, the method of predicting the time of ovulation and abstaining from exposure to conception during the "fertile period" surrounding that ovulation is generally referred to as the "rhythm method". The "rhythm method" has not proven to be a reliable method of birth control, primarily due to the inability of prior art methods to give advance "notice" of the onset of the fertile period. The desirability of improving the reliability of this method need not be discussed at length."

Lester's solution to the problem of predicting the time of ovulation, as described in U.S. Pat. No. 4,151,831, is to record and store basal body temperature measurements automatically and use such measurements to predict "the time of ovulation by a predetermined time interval, measured from the next predicted menstrual period by comparison" with the stored temperature measurements.

While this appears acceptable in theory, in actuality, the menstrual and/or ovulation cycles in many women are often not regular, thus a different mechanism is required than simply using a predetermined time interval from the next predicted menstrual cycle as suggested by Lester. Furthermore, fluctuations occur in basal body temperature which are independent of serum progesterone levels. Although the prior art U.S. Pat. No. 4,151,831 provides a mechanism to filter out the "noise" or inaccuracies associated with any given temperature measurement, it does not provide a mechanism to filter out the noise associated with the temperature measurements finally arrived at, taken as a whole over a number of days. For example a sore throat will cause a small rise in basal body temperature. While normally an increase in basal body temperature indicates ovulation, in this case it would not.

Also, from the viewpoint of a woman who is fertile but does not want to conceive, the basal body temperature method of birth control only works *after* ovulation and so abstinence is required for about two weeks out of each menstrual cycle.

A need therefore exists for a simple, inexpensive, non-invasive fertility status computer/indicator capable of accomodating to the particular menstrual cycle of the user and also capable of adapting to non-relevant fluctuations in basal body temperature (noise) measurements such as those induced by a sore throat or similar illness and which is capable of accurately predicting the time of ovulation in advance.

DISCLOSURE OF THE INVENTION

The present invention describes a method and apparatus which accurately predicts when ovulation is to occur. Accurate prediction of the time of ovulation is made on the basis of attributing values to a vaariety of parameters, specifically related to the user. These parameters comprise, in the main, (1) basal body temperature, (2) vaginal mucus change and (3) past menstrual cycle history. Basal body temperature measurements for determining the time of ovulation have already been discussed in connection with the description of the background art. Vaginal mucus change refers to a change in the cervical mucus from a dry, thick consistency to a wetter, more elastic consistency. It has been established that most women can sense this monthly change if made aware of it. Since this change occurs a few days prior to ovulation, its occurrence when properly combined with parameters 1 and 3 above, can serve as a basis for accurate forecast of time of ovulation.

In order to accomplish the foregoing, the user is provided with a fertility computer which enables the user to store historical information about herself in electronic codes in a plurality of storage devices, such as, bit registers. The information stored pertains to the following:

(1) The past menstrual cycle history, i.e., duration of recent menstrual cycles.

(2) Basal body temperature (BBT) history i.e., readings of the ten most relevant and recent BBT's.

(3) Information indicative of gynecological disorders, or discrepancies, such as, a menstrual cycle greater than 40 days or less than 20 days or spotting in the middle of a cycle.

(4) Information about the user's normal menstrual cycle activity, such as, current cycle number for which the device is being used (CN), the average cycle length (CL), current day number of the current cycle (DC), current day of the week (DW), day of the cycle (DM) resulting in a certain mucus level value (VM) from one to three, and the value of this particular mucus entry input, the number of valid temperature measurements taken and stored (TC) and the median BBT (MT) which is a weighted average BBT for a certain part of the cycle.

The information stored in these registers is then used, along with certain prediction indicators described below, to statistically predict when ovulation will occur. The prediction indicators comprise a series of switches operable by the user to input the fertility computer with information concerning the current status of certain of her body parameters. These prediction indicators enable the computer to take into account various gynecological disorders and irrelevant temperature readings and render a value judgment, much as a gynecologist is trained to do. Thus, these switches are used to indicate perturbations in temperature readings (such as may be caused by a sore throat), or the value or degree of mucus change, or spotting (i.e., blood in the vagina) in the middle of a menstrual cycle.

Also stored in the fertility computer are data from computed values of (a) fertility status FS, (b) pregnancy status PR, and (c) cycle error status ER. This data is in the form of electronic signals, such as binary data bits ranging, for example, from 0 to 255. A zero would indicate that the fertility status is lowest and a 255 that it is highest. The value FS indicates how likely it is for conception to result if intercourse occurs, PR is an assessment of whether the user is pregnant based on such factors as whether ovulation has occurred and, if so, has basal body temperature failed to drop and whether another period has commenced. The ER is an indication of the possibility of gynecological disorder. The typical factors used in computing ER are spotting (or bleeding in the middle of a cycle), a cycle that extends beyond 40 days or is less than 20 or whether there was a cycle error in the previous cycle.

A microprocessor within the fertility computer is programmed to process the above items of information in a predetermined manner and at the user's command to display either current fertility status, pregnancy status or cycle error status.

In summary, therefore, the apparatus of the invention comprises apparatus and processes for indicating and displaying the present fertility status of a female subject. It does this by storing information in respect to the female user's past history of length of cycle, basal body temperature and possible gynecological disorders plus her current menstrual cycle status, basal body temperature, fertility status and gynecological disorders. All of this information is processed in accordance with a predetermined program which ascribes certain values to each of the above parameters in order to predict the present fertility status of the user.

Thus, there is provided, in accordance with the invention, a quick, convenient, inexpensive and reliable method and apparatus for determining fertility status for use either as a birth control mechanism or as a device for enhancing fertility.

These and other advantages will become apparent from the following description.

BRIEF DESCRIPTION OF THE DRAWINGS

FIGS. 3a–3k is a flow-chart showing the logic steps associated with the invention.

BEST MODE FOR CARRYING OUT THE INVENTION

Definitions

Figure 1:
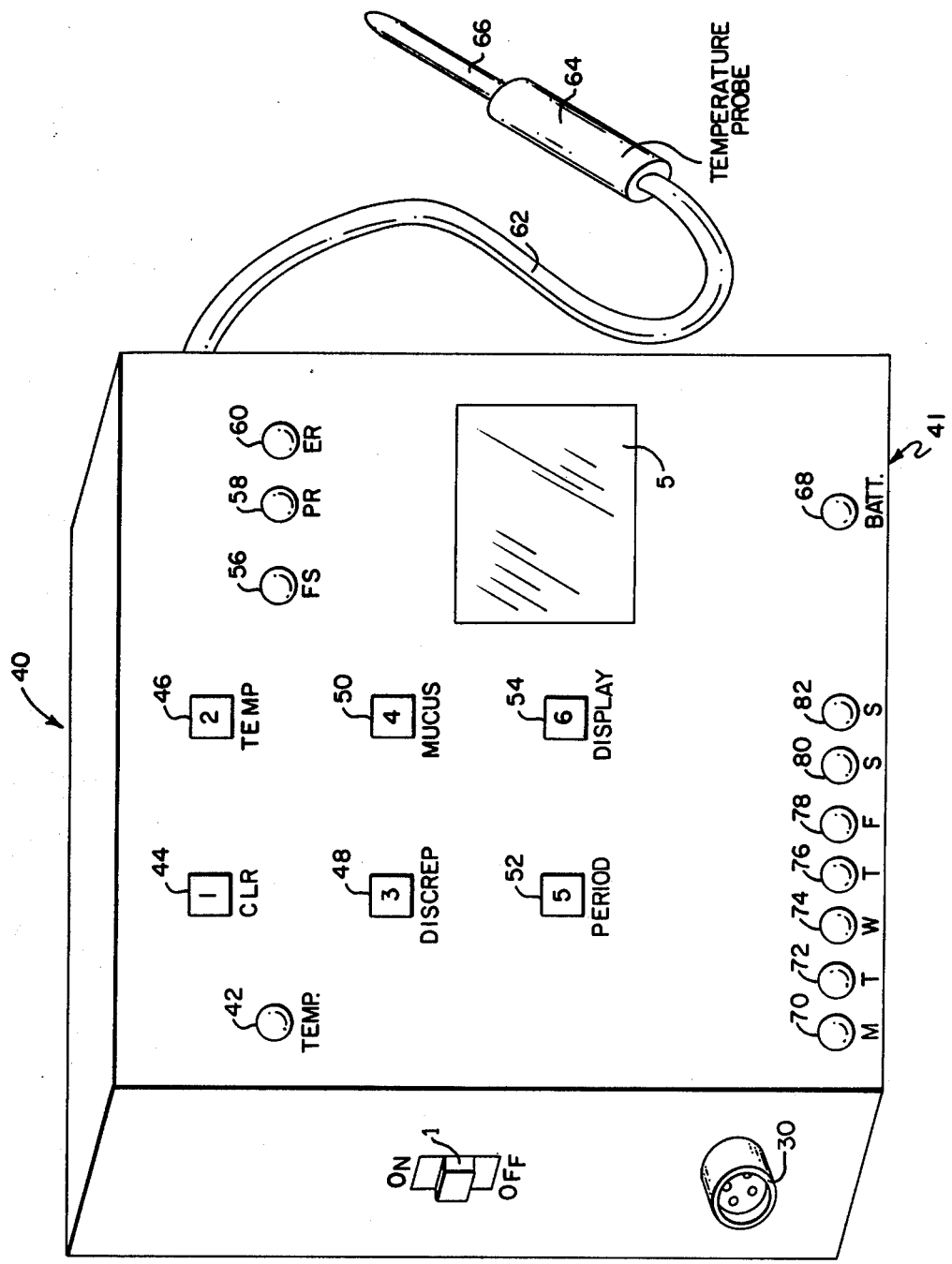
FIG. 1 is a perspective view showing the exterior configuration of a preferred embodiment of the invention.

For convenience, as used herein, the following terms, symbols and abbreviations are defined and summarized to mean:

| Symbol | Description | Numerical Limits | No. Bits Required |
|---|---|---|---|
| DW | day of week, Mon = 1, Sun = 7 | 0–7 | 3 |
| DC | day of cycle, first day = 1 | 0–41 | 6 |
| *CL | average cycle length minus 20 | 20.0–35.0 | 6 |
| C(1)– C(12) | C(1) is cycle 1 month ago C(12) is cycle 12 months ago each variable holds the length of that particular cycle below the average cycle length i.e., C(n)=0 if length C(n)> =CL C(n)=3 if CL−C(n)=3 C(n)=7 if CL−C(n)>7 | 0–7 | 3 × 12 = 36 |
| DM | day of cycle last 'mucus change' input | 0–41 | 6 |
| **VM | value of last 'mucus change' input | 0–3 | 2 |
| MT | median temperature | 0–255 | 8 |
| T(1)– T(10) | T(1) is most recent temp. input T(10) is temp input of approx. 10 days ago 2 bits per variable data stored as follows: high order bit - 1 if temperature crossed threshold low order bit - 1 if discrepancy level 1 entered | 0–3 | 2 × 10 = 20 |
| CN | cycle number (need when new unit) | 0–3 | 2 |
| TC | temperature counter (use with T() array) | 0–15 | 4 |
| F1 | flag 1 - cycle error, DC 40 days | 0–1 | 1 |
| F2 | flag 2 - cycle error, DC 20 days | 0–1 | 1 |
| F3 | flag 3 - spotting | 0–1 | 1 |
| F4 | flag 4 - previous cycle had F1, F2, or F3 set | 0–1 | 1 |
| F5 | flag 5 - temperature rise complete | 0–1 | 1 |
| F6 | flag 6 - most recent day had P-value set | 0–1 | 1 |
| F7 | flag 7 - temperature drop complete | 0–1 | 1 |
| LT | last temperature input entered | 0–255 | 8 |

-continued

| Symbol | Description | Numerical Limits | No. Bits Required |
|---|---|---|---|
| LP | last period input entered | 0-1 | 1 |
| LM | last mucus change input entered | 0-3 | 2 |
| LD | last discrepancy input entered | 0-2 | 2 |
| T(11)-T(14) | as above | 0-7 | 2×4=8 |
| F8-F14 | flags 8-14 | 0-1 | 7×1=7 |
|  |  |  | 128 bits (16 bytes) |
| ***DI | discrepancy value input (switch #3) | 0-2 | 2 |
| MI | mucus value input (switch #4) | 0-3 | 2 |
| PI | period value input (switch #5) | 0-1 | 1 |
| CI | clear current/last input (switch #1) | 0-3 | 2 |
| SI | display F-status input (switch #6) | 0-1 | 1 |
| TT | temperature value measured (A/D #1) | 0-255 | 8 |
| TI | temperature entry input (switch #2) | 0-1 | 1 |
| SS | sensitivity value measured (A/D #2) | 0-255 | 8 |
| RR | timing value (A/D #3) | 0-255 | 8 |
| BB | battery value (A/D #4) | 0-255 | 8 |
| SN | switch no. hit | 0-6 | 3 |
| FS | fertility status (red LED #1) | 0-255 | 8 |
| PR | pregnancy status (red LED #2) | 0-255 | 8 |
| ER | error status (red LED #3) | 0-255 | 8 |
| FD | DW to flash corresponding to coming period | 1-7 | 3 |
| DF | differential value | 1-41 | 6 |
| TV | temporary variable | 0-255 | 8 |
| Q1 | temporary flag 1 | 0-1 | 1 |
| Q2 | temporary flag 2 | 0-1 | 1 |
| Q3 | temporary flag 3 | 0-1 | 1 |
| Q4 | temporary flag 4 | 0-1 | 1 |
| Q5 | temporary flag 5 | 0-1 | 1 |
| LC | temporary loop counter | 0-63 | 6 |

NOTES:
*To save space when "read" CL add 20 and when "write" CL subtract 20 To do so takes 4 bits if CL is to vary from 20-35, however, 6 bits are provided for a 'pseudo-decimal' point. This will increase the accuracy of subsequent average calculations. In summary, CL is read as follows: CL=20+INT(CL)+.5)
**The input VM is entered whenever the dry to wet cervical mucus change is sensed; a "1" is entered if the user thinks change occurred. a "3" is entered if the user is very sure change has occurred.
***A discrepancy level 1 is entered if taking temperature a few hours later than normal, etc. and a discrepancy level 2 if user wakes up with a sore throat, etc.

The term "numerical limits" means the value inputs that may be entered into storage. The number of bits used to store the value inputs are indicated adjacent each limit.

External Configuration

Turning now to FIG. 1, there is shown a preferred embodiment of the external configuration of the fertility computer.

The fertility computer 40 is enclosed in a small case 41. This case includes in the interior, the various computer chips and printed circuit boards making up the heart of the computer and, in addition, contains batteries for supplying power to the electronic chips. Mounted on the outside of the enclosure 41 are six momentary push-button switches 44, 46, 48, 50, 52 and 54. A yellow LED light (light emitting diode light) 68 is provided to indicate whether or not the fertility computer and the battery are operating properly. This light will be "off" if the device is not operating properly.

Seven yellow LED lights 70, 72, 74, 76, 78, 80 and 82 are provided to display the day of the week. Monday is displayed by light 70, Tuesday by light 72 and so on to Sunday, which is light 82. These lights are also employed to indicate when the user is plus or minus seven days from the beginning of an expected period, in which case, the appropriate LED will flash.

A green LED 42 is provided which flashes during temperature measurement so that the user is prompted to maintain the temperature probe in her mouth. Three red LED's 56, 58 and 60 are provided to indicate respectively the fertility status (FS), pregnancy status (PR) and error status (ER). At a level zero input, the LEDs are "off", at a level 63 input the LEDs flash at a one cycle per second rate and at a maximum level of 255, the LEDs flash at a four cycle per second rate.

Switches 44, 46, 48, 50, 52 and 54 are respectively the clear current/last entry switch, take temperature measurement switch, discrepancy entry switch, mucus entry switch, period entry switch and display fertility status entry switch.

An On-Off switch 1 is provided to switch the power from the batteries (not shown) to the fertility computer 40. A temperature probe 64 is also coupled to the fertility computer 40 via cable 62 to enable basal body temperature measurements from temperature sensor 66 to be input to the fertility computer.

Instructions for using the device may be conveniently printed in the space provided at 5.

Functional Description

Figure 2:
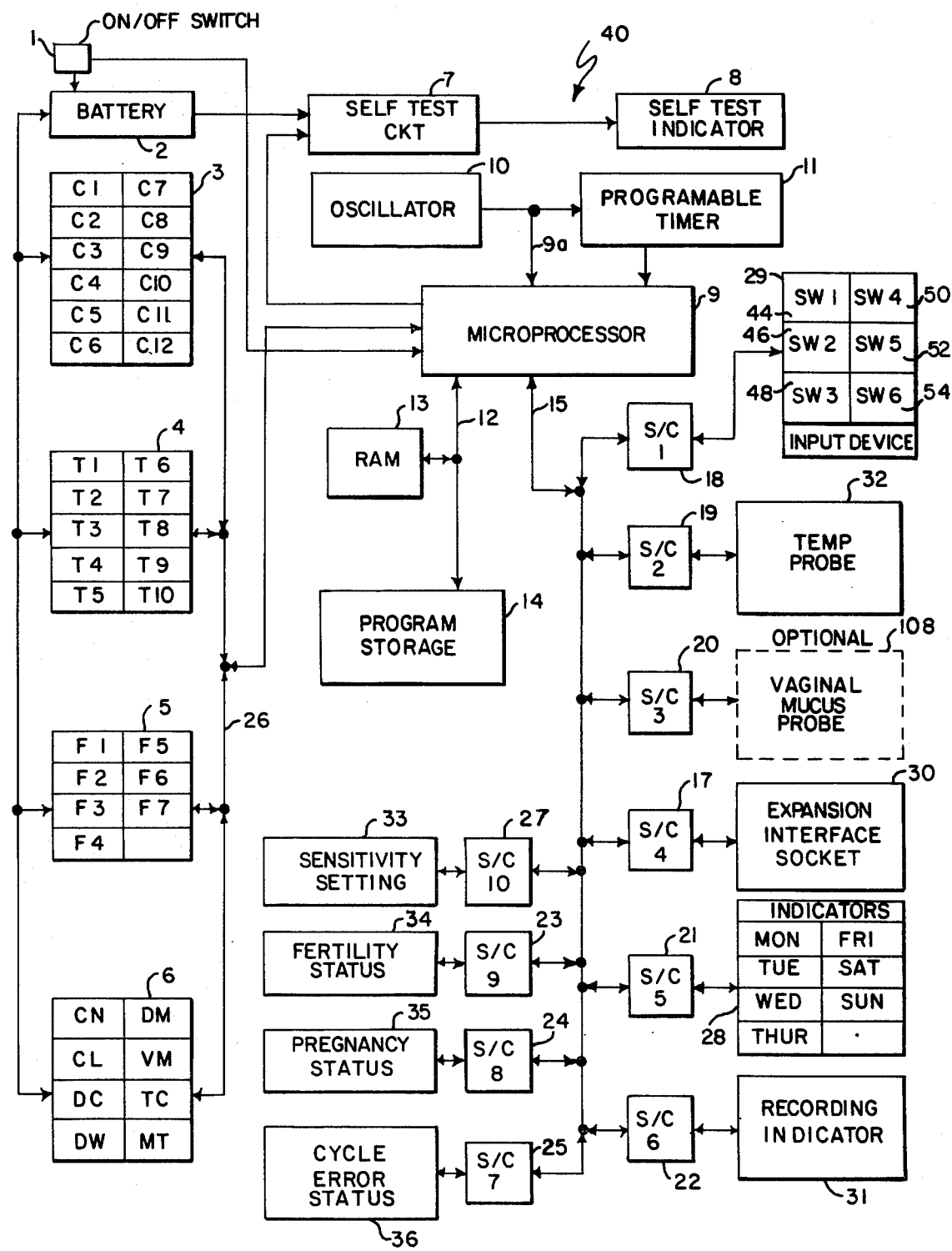
FIG. 2 is a block-diagram of the invention.
Figure 3A:
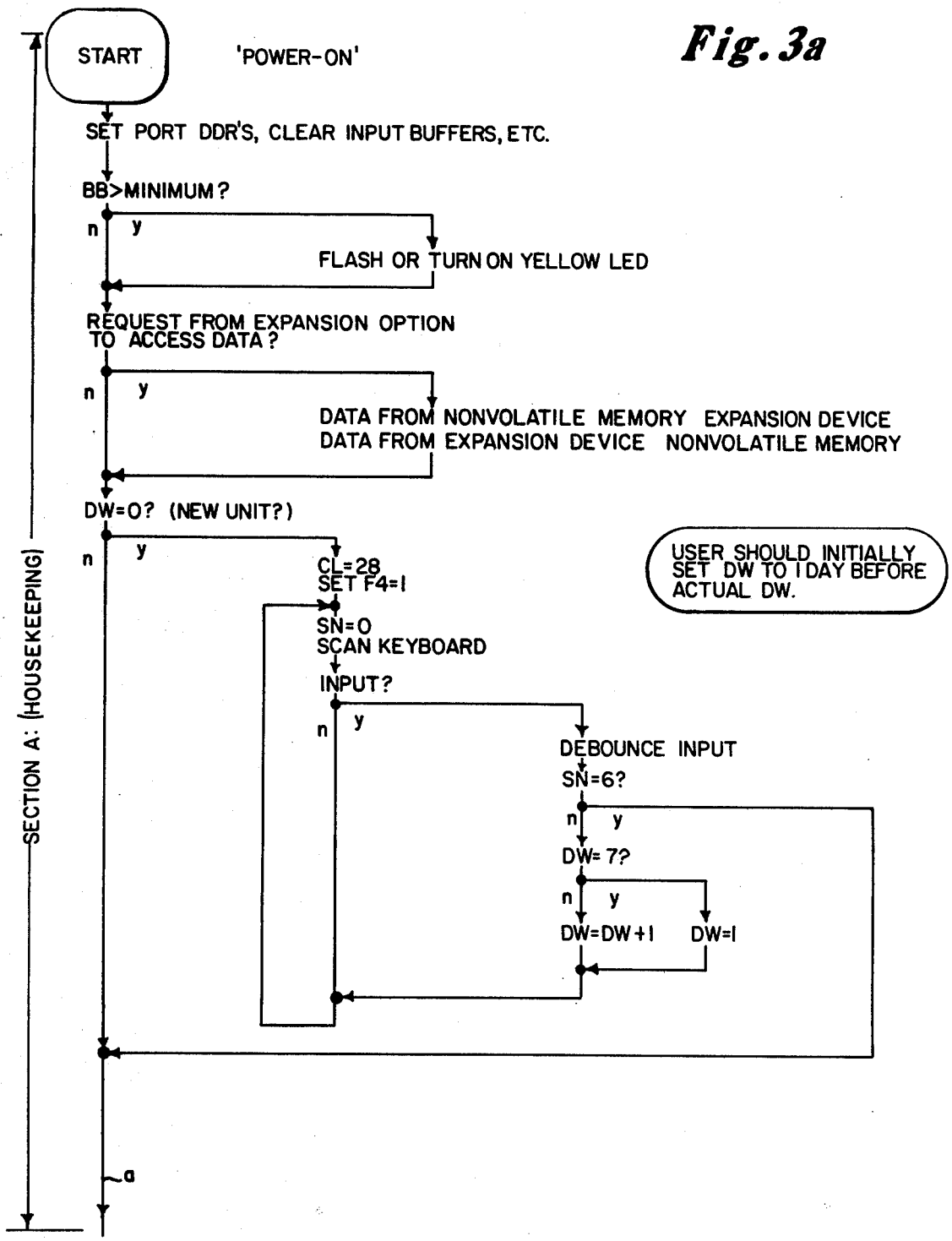
Figure 3B:
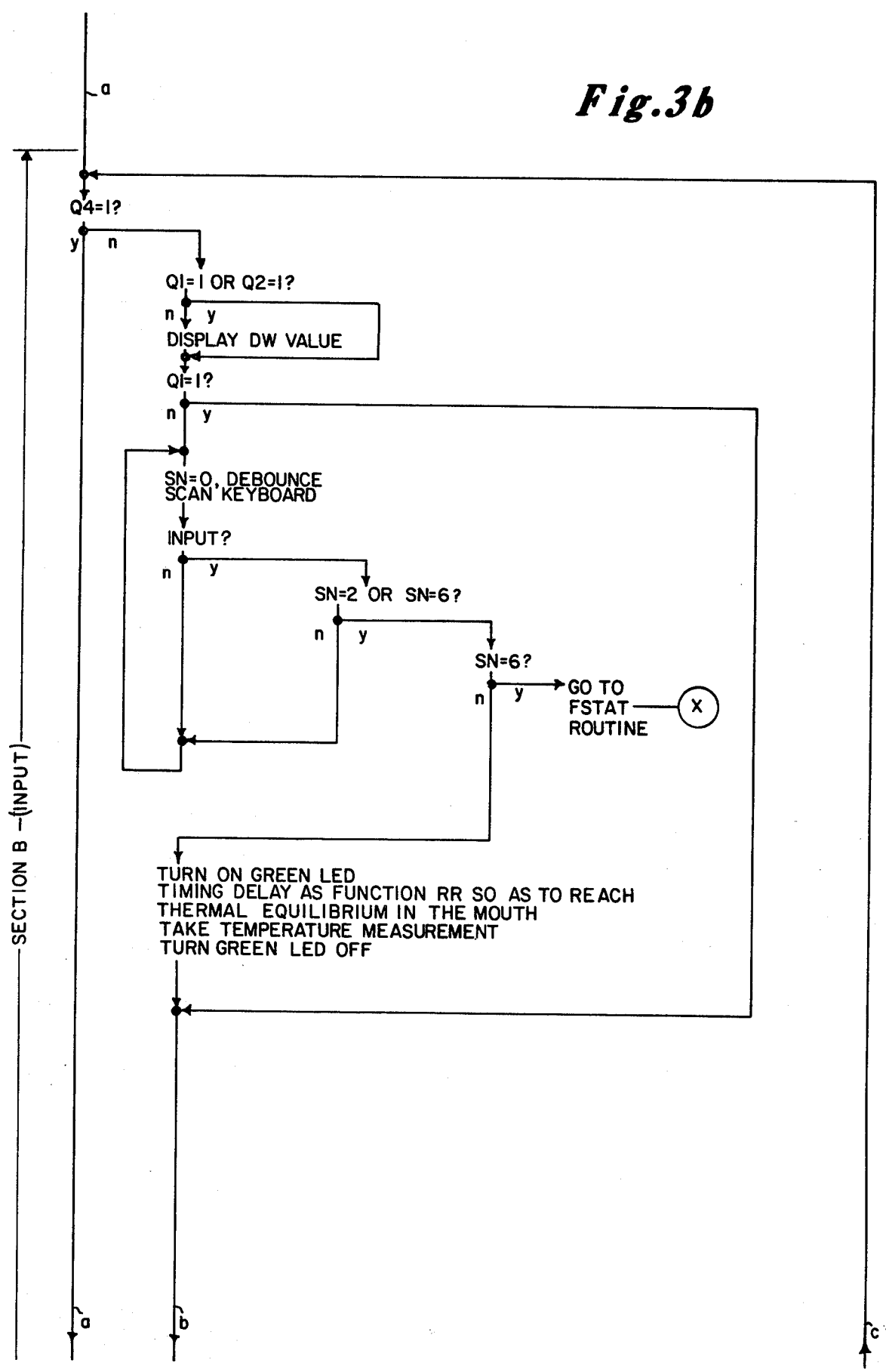
Figure 3E:
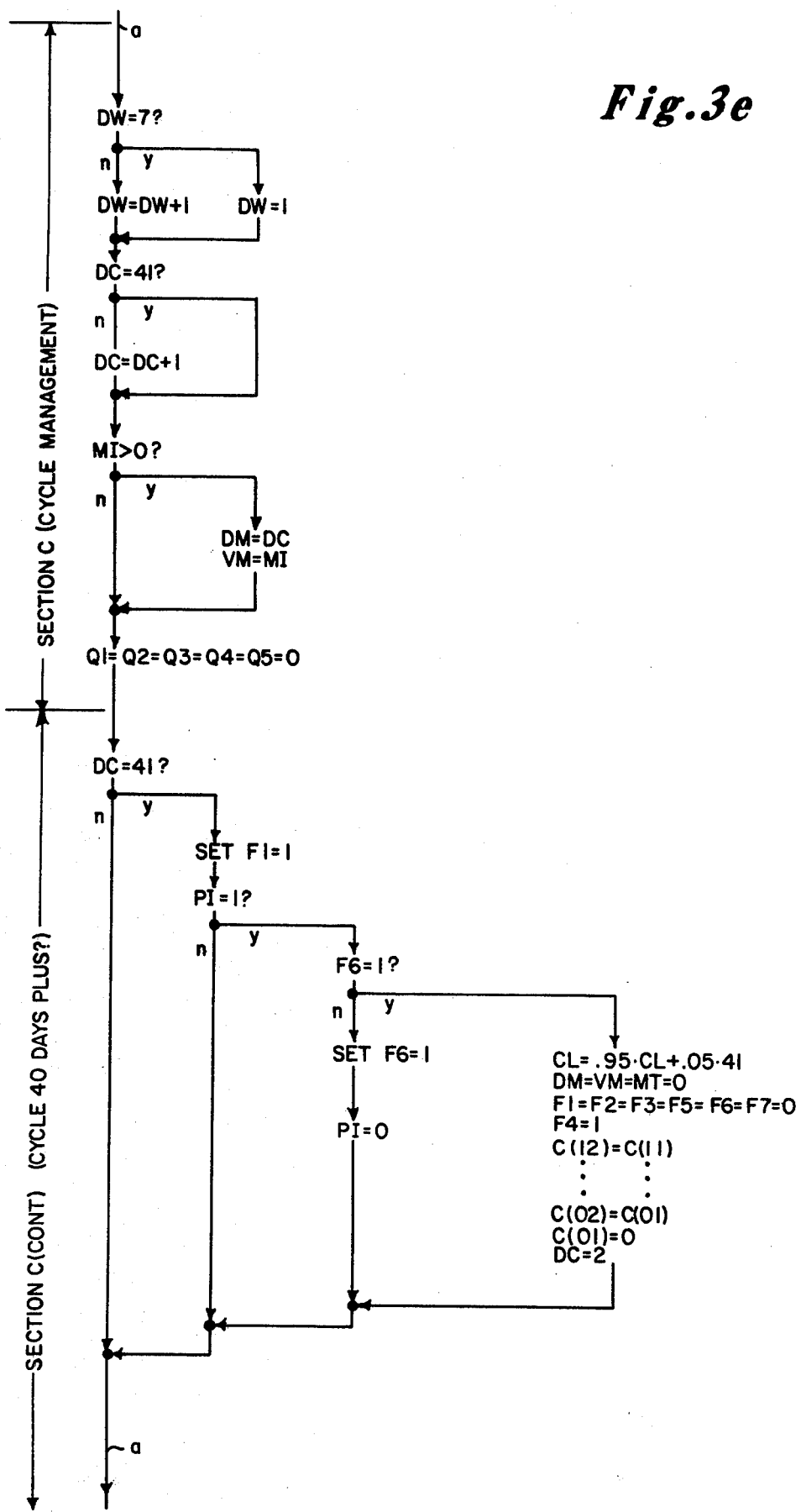
Figure 3F:
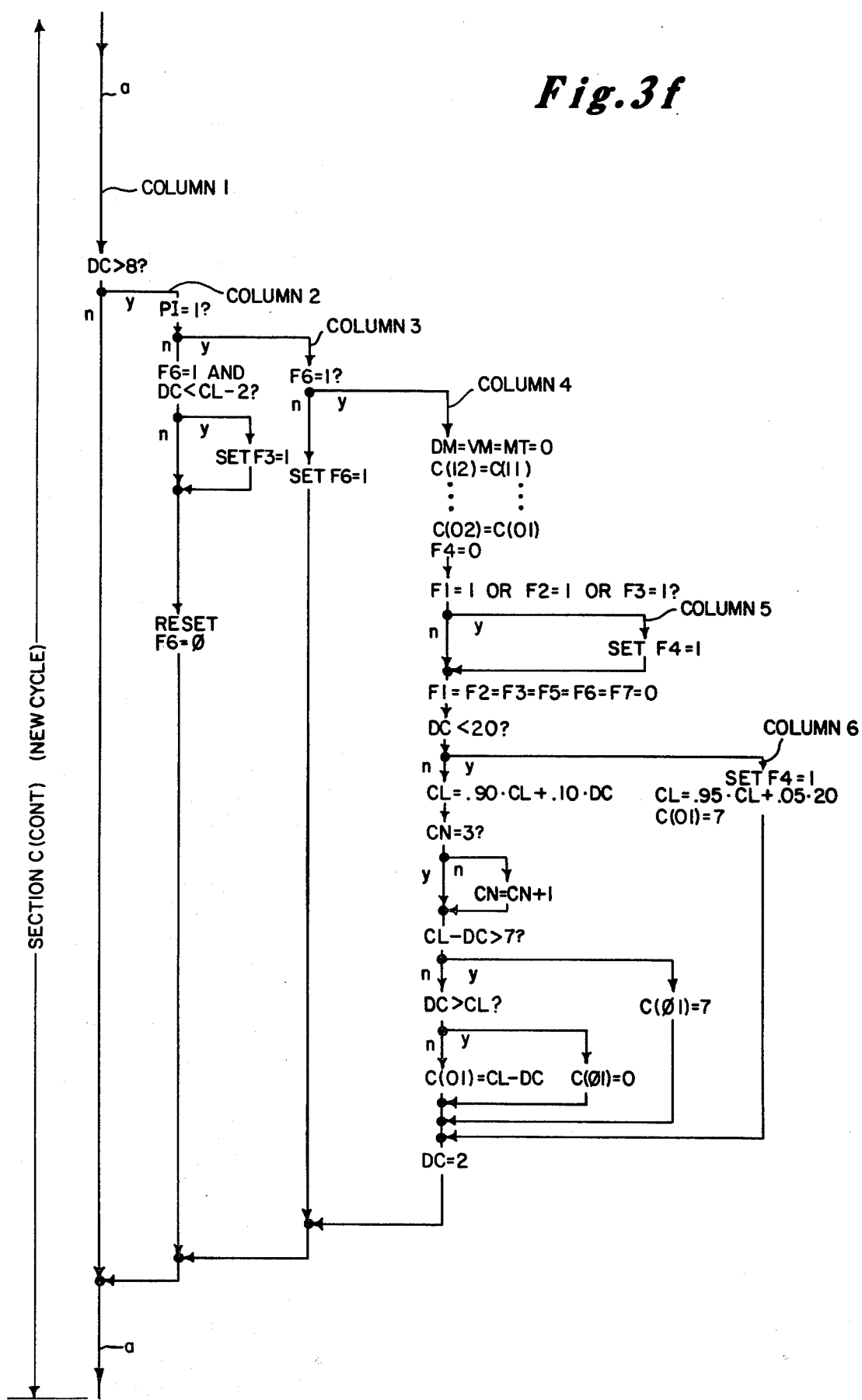
Figure 3G:
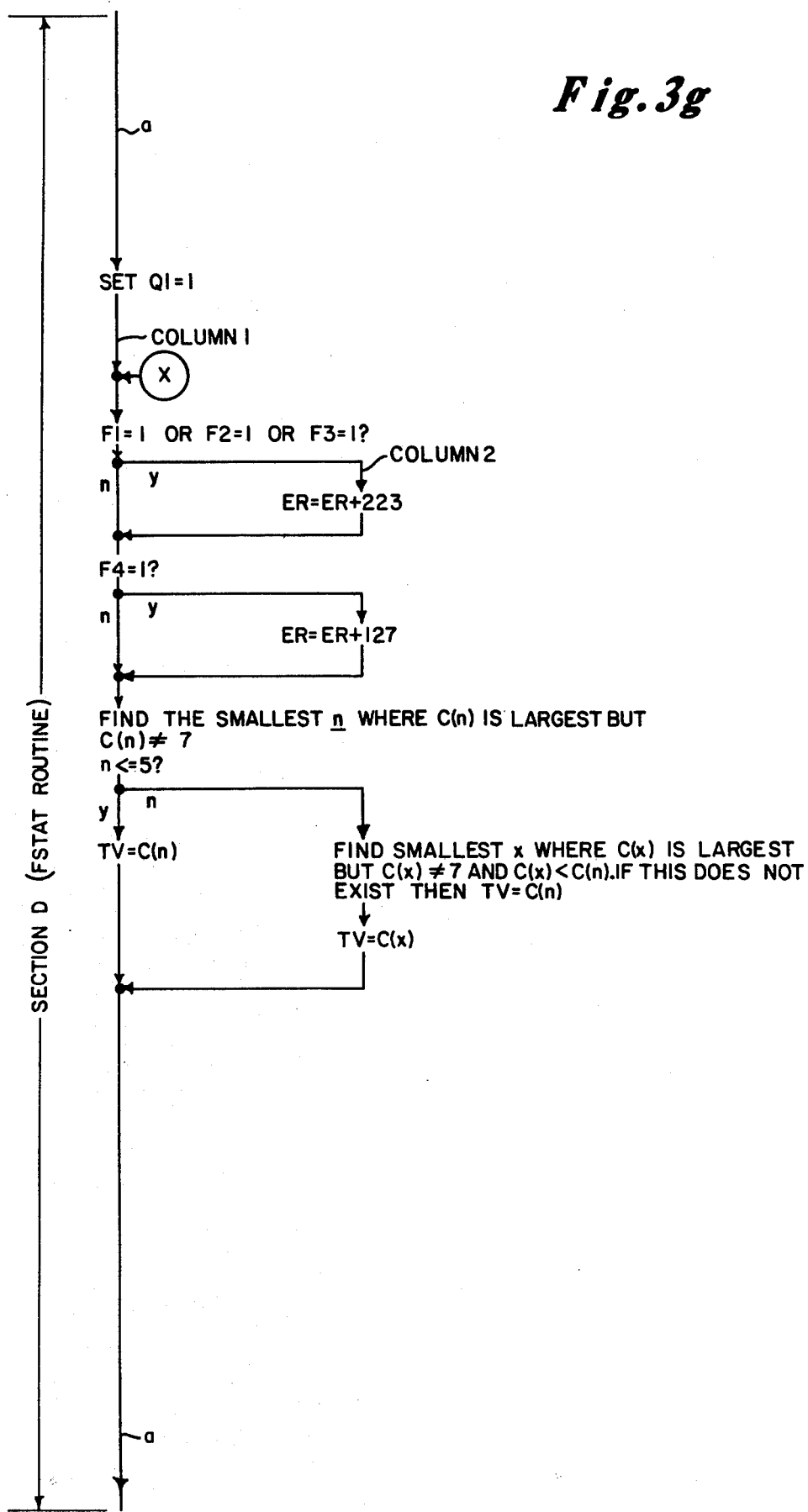
Figure 3H:
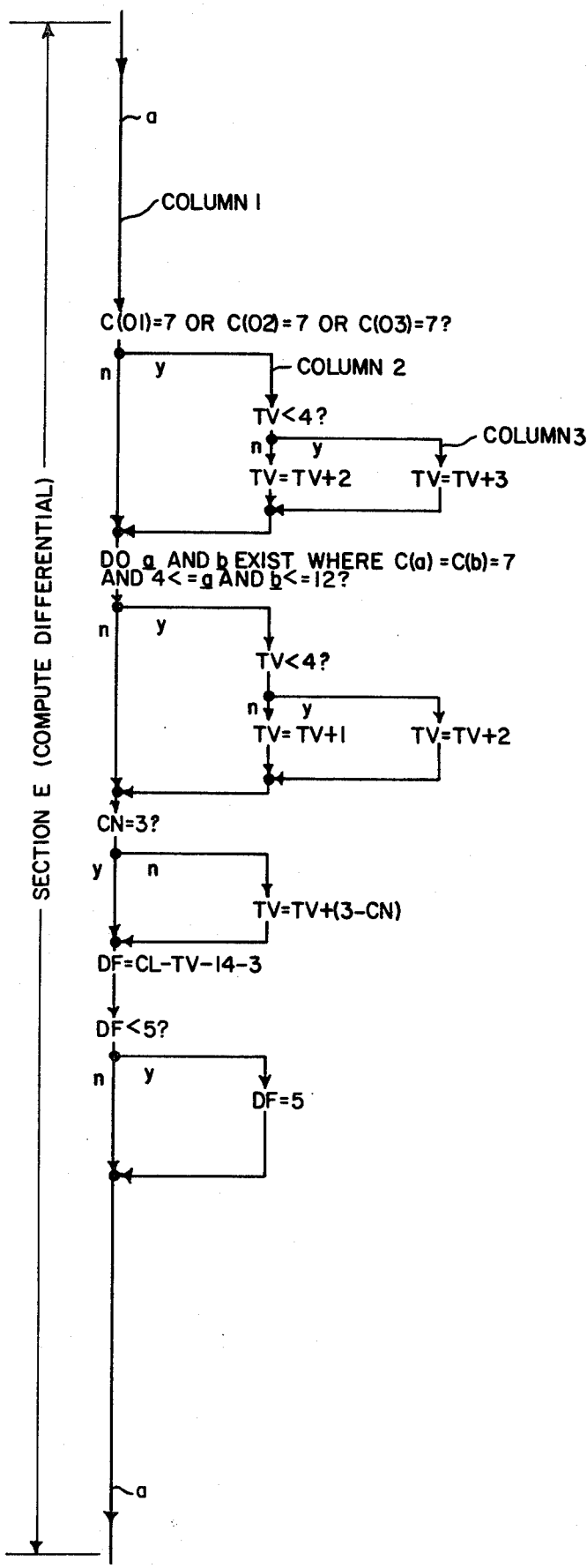
Figure 3I:
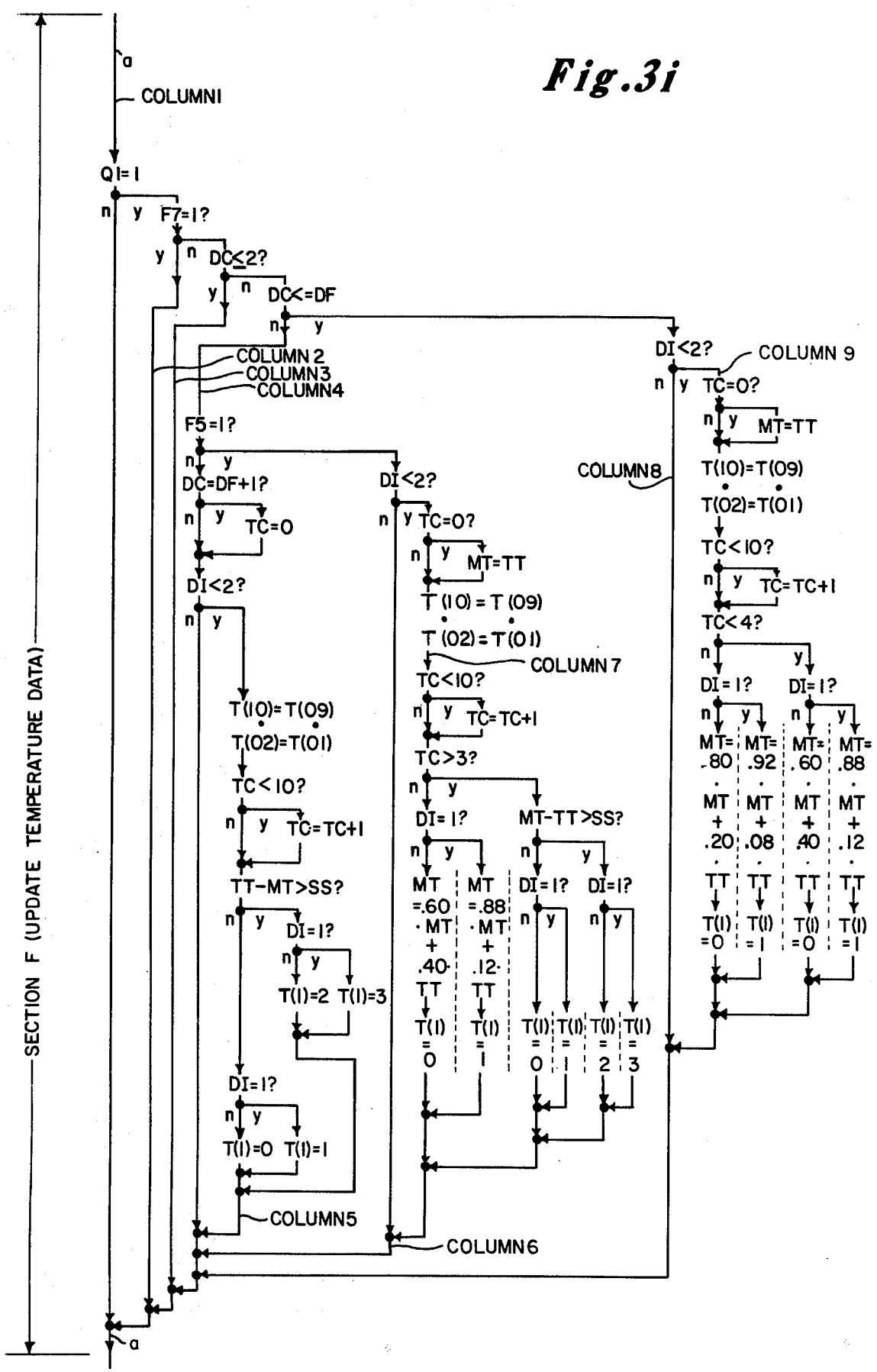
Figure 3J:
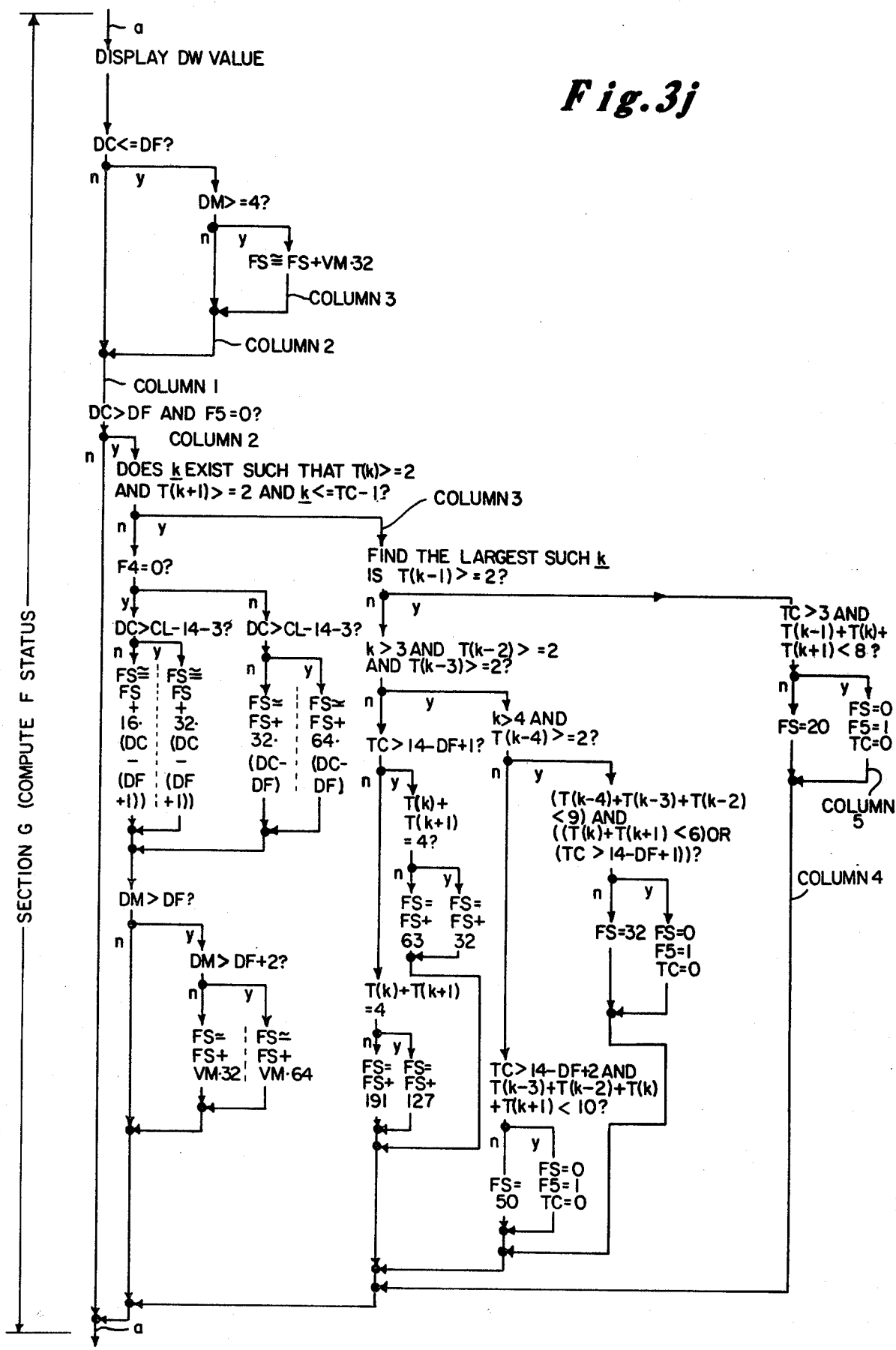
Figure 3K:
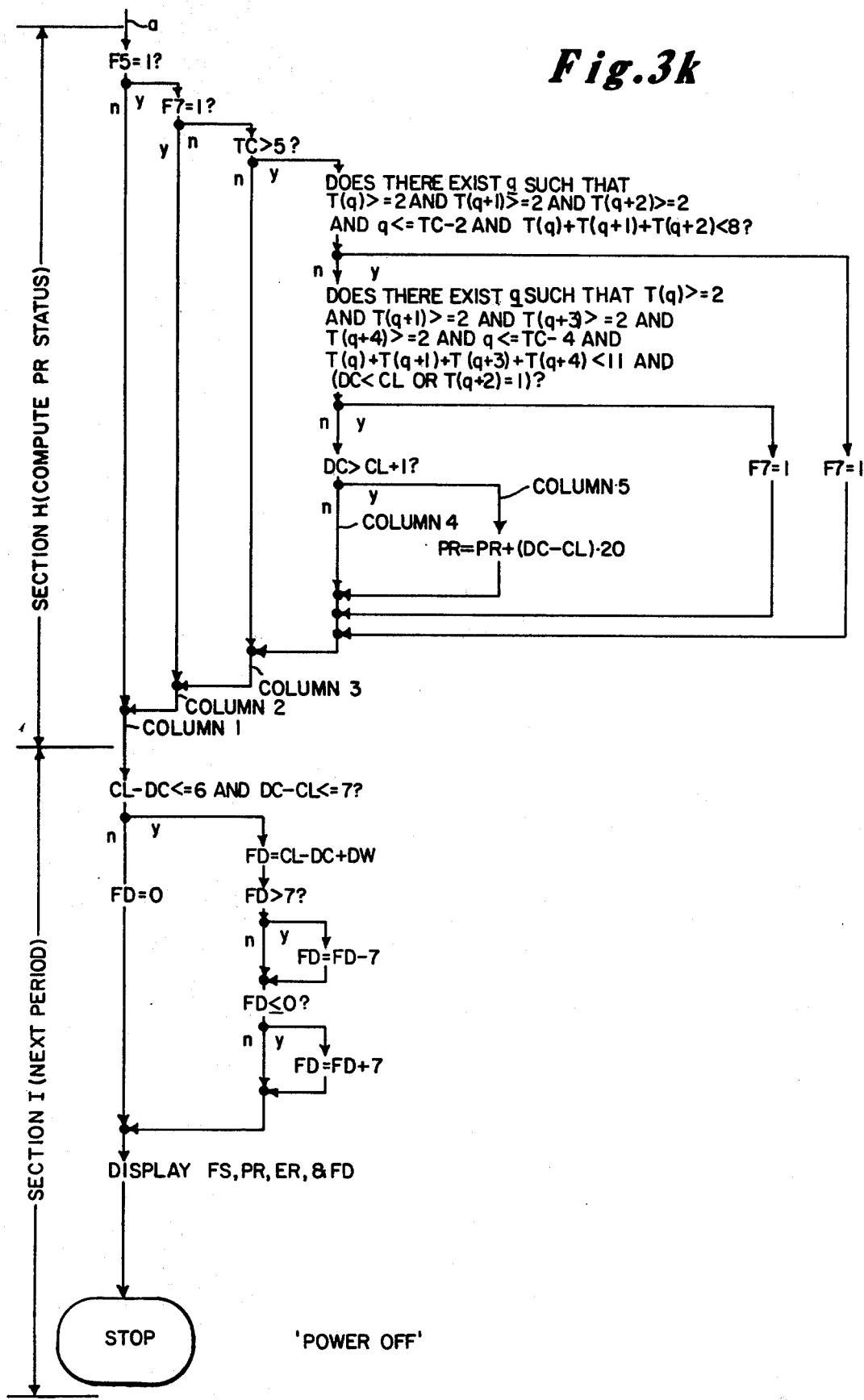

The internal electronics for the fertility computer 40 are shown in block diagram form in FIG. 2.

When the fertility computer 40 is turned on by the "On/Off" switch 1, the battery 2 voltage is applied to all the structures shown in FIG. 2. Register groups 3, 4, 5 and 6 are well known non-volatile storage registers in that the battery voltage is applied to these components even when the fertility computer 40 is "off", and so, they do not lose their contents. This is presently the most economical route to take although advances in microtechnology will soon produce economical non-volatile registers that require no standby power source. Upon power initiation, the microprocessor 9 follows a general self-test algorithm which ensures that all components are in working order. Assuming that the latter is true, the microprocessor 9 indicates this to the self-test circuit 7 which will, if the voltage from battery 2 is sufficient, indicate correct operation via the self-test indicator 8. Indicator 8 is a yellow LED (light-emitting-diode) which flashes at approximately 1 Hz if all is functional.

The microprocessor 9 is coupled via line 9a to an oscillator 10 and a programmable timer 11. The timer serves to count a number of cycles from the oscillator and lets the microprocessor 9 know; thereby serving as a clock mechanism to insure proper timing of signals through the microprocessor. Also coupled to the microprocessor is a data/address bus 12, a RAM (random-access-memory) storage 13 and ROM (read-only-memory) program storage 14. Although program storage can be accomplished in RAM, as is the case in larger, general purpose computer systems, for smaller, more specialized electronic devices as used herein, it often proves more economical to store the program permanently in a form of ROM, such as, PROM, EPROM, EEPROM, etc. RAM 13 is used to store intermediate results of computations and is required by the microprocessor 9 because the latter can only work on one operation at one time. It is possible that if discrete logic building blocks were used instead of the microprocessor 9 then the RAM 13 may not be necessary.

The I/O (Input/Output) bus 15 is a typical feature of microprocessor systems and serves to route the I/O signals to and from microprocessor 9. After the self-test algorithm, which is programmed into the microprocessor, is executed by the fertility computer, the microprocessor 9 checks to see if there is any input from the expansion interface socket 30 through S/C (signal conditioner) #4 numbered 17 in FIG. 2. The signal conditioners transform the input signals from the external devices to a signal which can be handled by the I/O bus 15 and vice versa. Also, the signal conditioners accomplish low-level processing as required. The expansion interface socket 30 allows the microprocessor 9 to be connected to a variety of devices. Although these may include additional sensory probes, additional I/O devices, such as a voice circuit for blind people perhaps, it generally will be used by a doctor to access and display, and change if necessary, the contents of register groups 3, 4, 5 and 6. For example, instead of the fertility computer 40 having to learn on its own a woman's gynecological and physical history, a doctor (or a woman user if she was capable) would enter this information directly into the register groups. Likewise, on an office visit to her physician, the doctor could attach his general purpose computer to the expansion interface socket 30 and examine the contents of the register groups.

If there is an input from S/C #4, then the microprocessor sequentially dumps the contents of register groups 3, 4, 5 and 6 into a contiguous area of storage memory in the device which is interfacing with the expansion interface socket 30. The external device (not shown) then displays, prints or modifies, or any combination of these operations, the information in its RAM area. The external device can then allow, or make by itself, any changes in the contents of its RAM area which now hold the contents of register groups 3, 4, 5 and 6. When it is ready, the external device then sequentially loads the expansion interface socket 30. S/C #4 (17) indicates this to the microprocessor 9 which then sequentially takes the data it is receiving from the expansion interface socket 30 and loads it sequentially into register groups 3, 4, 5 and 6. Other variations of inputting an external device might include an external device and a corresponding algorithm in the fertility computer capable of addressing and thus accessing specific registers in the various register groups 3-6. Furthermore, S/C #4 17 could be adapted to recognize various external attachments and indicate this to the microprocessor 9 so that the latter could choose the appropriate algorithm to follow, e.g., a certain algorithm for use with the physician's general purpose computer and another algorithm for use with an external vocalization circuit.

Unique to the fertility computer is the F-bus 26. This bus connects the microprocessor 9 to the register groups 3, 4, 5 and 6. Register groups 3 and 4 consist of twelve and ten byte-wide registers respectively. Register group 5 consists of seven byte-wide registers used as flags. Register group 6 consists of eight byte-wide registers. The size of these register groups could be reduced even further, as indicated by the storage space requirements shown above. Register group 3 stores information concerning the length of the twelve most recent menstrual cycles C1-C12. While there are a variety of possible formats which could be used, in the embodiment being described herein, if the cycle length CL is equal to or greater than the average cycle length, a value of zero is stored in the appropriate register in register group 3. If the difference of the average cycle length minus the cycle length in question, is equal to or greater than seven, then a value of seven is stored, otherwise a value equal to the difference is stored in register group 3.

Register group 4 stores information concerning the basal body temperature readings of the ten most relevant and recent days. Again, a variety of formats are possible but the one used in this embodiment is as follows: a zero is stored if the temperature readings have not crossed threshold (Note: Threshold is defined as the condition when the appropriate difference between MT and TT is greater than the value of SS.), a one is stored if the temperature readings have not crossed threshold but a discrepancy level one (i.e., discrepancy button 48 hit once) has been entered, a two is stored if the threshold has been crossed and no discrepancy has been entered and a three is stored if the threshold has been crossed and discrepancy level one entered.

It should be emphasized that the fact that the temperature readings are coupled with the discrepancy entries, forms part of the mechanism previously described, which enables inaccurate temperature measurements to be discriminated against as a whole and filtered out. Register group 5 serves as a grouping for seven one-bit flag registers. A "flag" is a value stored in the register which indicates the occurrence or non-occurrence of an event. Flag F1 is set if a cycle is greater than forty days. Flag F2 is set if a cycle is less than twenty days. Flag F3 is set when spotting occurs during a cycle. Flag F4 is set if either of the previous three flags were set during the previous month. Flag F5 is set if a temperature rise indicating ovulation is achieved. Although not shown in FIG. 2, this flag F5 could be attached to an indicator which would tell the user that ovulation had occurred. Flag F6 is set if a period level one input has been entered into the microprocessor 9 from switch 5 (52) of input device 29. Flag F7 is set if a basal body temperature drop occurs after the ovulatory temperature rise has been achieved.

Register group 6 contains various miscellaneous registers required for the operation of the fertility computer 40. CN is the present cycle number, e.g., if CN is equal to two and then a new cycle begins, CN is incremented by one to a new value of three. CL is the average cycle length which, as shown later, is really a weighted average in order to filter out irrelevant cycles. DC is the current day number of the current cycle. DW is the current day of the week.

Although various elegant techniques, as later discussed, can be used to advise the user that it is time for another basal body temperature reading, for reasons of economy, the following day of the week system is used in this embodiment.

Indicators 28 indicate what day of the week it is. Seven yellow LED's are used, 70, 72, 74, 76, 78, 80 and 82 (FIG. 1), corresponding to each day of the week. It is recommended that the user record her basal body temperature daily. Therefore, if the user wakes up on Friday morning, for example, she will see that the day of the week indicator 28 indicates that the day of the week is Thursday. Thus the user will know she must take her basal body temperature. As will be explained later, to do this, the microprocessor 9 automatically increments the DW register (or if it previously was Sunday, sets it back to a value of one, corresponding to Monday) of stack register 6. Thus, when the microprocessor 9 later commands S/C #5 21 to display the day of the week corresponding to the value in DW of 6, the indicators 28 will now, to continue the example above, indicate Friday, and so, the user will know for the rest of the day that no further temperature measurements are required.

DM in register 6 is the day of the cycle that most recently resulted in a mucus level one to three input entry. VM is the value of this particular mucus input entry. Together, DM and VM form part of the mechanism in the present invention which allows accurate prediction of when ovulation is to occur, not simply when ovulation has already occurred or a prediction of when ovulation is to occur by a predetermined time interval, as is the case with the prior art.

The medical literature indicates that a few days before ovulation is to occur, there is a change in cervical mucus from a dry, thick consistency to a wetter, more elastic consistency. Most women can sense this monthly change if made aware of it and so can indicate that it is occurring to the microprocessor 9 via an input device 29, e.g., a keypad. If the user is not sure of this change in consistency of the cervical mucus, she can make use of an optional vaginal probe 108, which is especially designed to automatically measure such changes. The prior art (specifically U.S. Pat. Nos. 4,013,066, 3,926,037, 4,151,833, 3,749,089 and 4,036,212) give examples of the mechanisms and structures required in such a probe. Thus, the combination of DM, VM in register 6, the input device 29 and (optional) vaginal mucus probe 108, along with the microprocessor 9 as the controlling element, form a structure which serves in the present invention to predict when ovulation will occur on the basis of the status of dynamic body parameters.

TC is used by the microprocessor 9 in conjunction with register group 4 and serves to tell which is the last register in register group 4 containing valid information. This is necessary because when temperature values must be stored in register group 4, first register T1 is used. Then the next day the contents of T1 are shifted to register T2 while the new present day contents are entered into T1. At this point, TC would contain a value of two indicating that only T1 and T2 are filled with valid information. TC is necessary, since the filtering out of irrelevant temperature measurements precludes a one to one relationship between the day of the cycle offset at some relevant day and the number of registers in group 4 filled with relevant contents. MT is the median temperature and is the weighted average temperature for a certain part of the cycle. The particular weighting system will be shown in connection with FIG. 3. The use of a weighted average tends to enhance the filtering mechanism for avoiding irrelevant temperature readings. Together, the group of registers 3, 4, 5 and 6 are used in a statistical sense to form a mechanism which statistically predicts when ovulation is to occur. A system is provided to combine this statistical mechanism with the mucus-change mechanism described before, in order to allow the most accurate prediction of when ovulation is to occur.

Logic Description

The remaining items shown in FIG. 2 may be best described in connection with their function, as shown in the Logic Flow Charts of FIG. 3. This Flow Chart shows the step-by-step operations which are performed by the apparatus in FIG. 2 in response to various inputs and as controlled by the program stored in memory. The symbols used are previously defined above. The reference numerals will be to elements in FIGS. 1 or 2.

Figure 4:
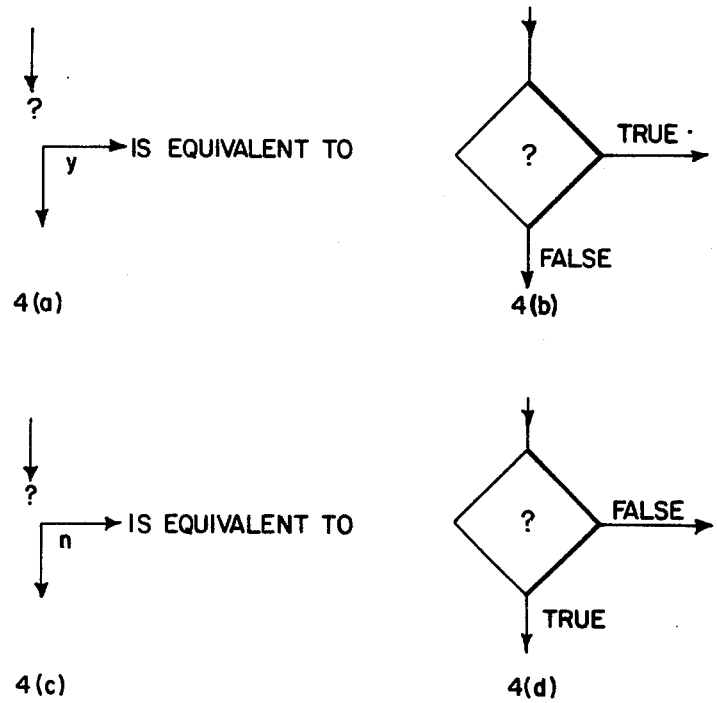
FIG. 4 depicts the logic symbols used in FIG. 3.

Before proceeding to FIG. 3, we must briefly turn to FIG. 4 which shows the logic symbolism used in FIG. 3. As can be seen in FIG. 4, the logic of 4(*a*) is equivalent to 4(*b*) and the logic of 4(*c*) is equivalent to 4(*d*). Thus, in following the FIG. 3 chart, if the answer to the question/value inputted at a node is "true/present", then an arrow marked y (yes) would be followed. Conversely, if the answer/value is "false/not present", then an arrow marked n (no) would be followed.

Housekeeping Logic

Referring now to Section A of FIG. 3, this shows how the Housekeeping routine is implemented. When the power is turned on to the fertility computer 40 by ON-OFF switch 1, a program in the microprocessor 9 directs the input buffers to be cleared and enables the data registers to be addressed. The battery voltage is checked and if correct, LED 68 lights up.

Through the F-bus 26, the microprocessor 9 accesses register DW of group registers 6 to determine if it contains a non-zero value. If it does contain the value of zero, this indicates that the fertility computer has not been used before. If so, the microprocessor 9 places a starting value of 28 in register CL of group 6 and sets flag F4 of group 5. The user then enters, through input device 29, the desired day of the week which the microprocessor 9 will then store as input data in register DW of 6.

Input Logic

Referring now to Section B of FIG. 3, the next thing the fertility computer does is display or indicate via indicator 28, the day of the week corresponding to the value of DW in group register 6. At this point, the fertility computer asks the user if she wishes to simply find out her fertility status or if she wishes to record her basal body temperature or other relevant body parameters. If the former is chosen, then the microprocessor 9 jumps to the series of algorithms used to determine fertility status which are discussed below in connection with Section D of FIG. 3. Otherwise, the microprocessor 9 indicates to the user via the recording indicator 31 that a temperature measurement is in order. Indicator 31 is simply a LED. While a number of ways are suggested in which human body temperature can be measured, the present embodiment uses a simple temperature sensing probe 32, such as, an inexpensive thermocouple, thermistor, or temperature sensitive semiconductor. An inexpensive temperature sensor can be used because the structure of the fertility computer, and in particular register group 4, is arranged to process relative differences in daily basal body temperature rather than absolute temperature values. If accurate absolute temperature readings are required, then an expensive temperature sensor with an accuracy of 1/10°-1/20° F. is required. This rather rigid requirement is dispensed with in the present invention because, as mentioned above, the structure of the fertility computer is arranged to process relative differences in temperature. Whether the temperature probe 32 indicates 94° F. or 99° F. is unimportant. Rather, the significance in a temperature reading lies in its relationship with its neighbors in group 4, i.e., day to day repeatability is the important criteria, so that when a *change* in temperature does occur, it can be noted.

Although the medical literature indicates that it is best to measure basal body temperature per vagina or per rectum, and although this approach may be taken quite easily with the present embodiment, the embodiment also allows the user to record oral basal body temperatures. The error rate of temperature readings taken sublingually, as opposed to vaginally or rectally is probably somewhat higher. However, due to the extensive signal conditioning and filtering capabilities of the present invention, this should not be a problem in actual practice. While not shown in the present embodiment, it would be possible to have an algorithm which would allow the user to alternate from oral temperature readings to vaginal temperature readings whenever she desired to do so. As it stands now, the present embodiment of the fertility computer requires that the user measure vaginal temperature or oral temperature, but not both during the course of a single cycle.

As anyone who is skilled in the art of heat transfer recognizes, thermal equilibrium does not occur instantaneously but rather can be approximated only after a certain number of time constants. So that there is consistency in day to day temperature measurements some means of alerting the user to keep the temperature probe in a functional position for a certain time period is required. For reasons of economy in the present embodiment, this is accomplished by recording indicator 31 which is a simple LED which stays on or flashes until sufficient time has elapsed for a valid temperature recording to be taken. The recording indicator 31 may also be used with other probes, for example, with the vaginal mucus probe 30, the indicator telling the user to keep the probe in a functional position until a valid reading is obtained. S/C #2 19 not only converts the analog signal from the temperature probe 32 to a digital signal which is acceptable to the I/O bus 15 but is responsible for the first level of filtering out of irrelevant temperature readings. While the prior art suggests a multitude of approaches for analog to digital conversion, for reasons of economy, an inexpensive capacitor-charging-ramp technique can be used. Although this technique produces non-linear results, it is very reliable and repeatable. An algorithm can be used by the microprocessor 9 to correct for these non-linearities. However, the point to be emphasized is that such a technique is suitable for use with the fertility computer because register group 4 and other structures therein are adapted to consider changes in day to day basal body temperatures rather than the absolute values of the temperature readings.

S/C #2 19 performs the first level of filtering out of irrelevant temperature readings. When the temperature probe 32 indicates that it is within a certain distance of normal body temperature (e.g., ninety-degrees) S/C #2 19 indicates this to the microprocessor 9. Thus the microprocessor 9 can begin timing the period required for thermal equilibrium to be reached. At the end of this period S/C #2 19 is programmed to measure the temperature reading. If the reading is an unreasonable one, i.e., too low or too high, then S/C #2 19 may take a series of temperature measurements and average them before returning a value to the microprocessor via I/O bus 15. As well, S/C #2 19 checks to make sure that during the period of attaining of thermal equilibrium there are no significant "up/down" fluctuations in temperature indicating that the temperature probe has been moved from its functional position. If the latter occurs, then S/C #2 will repeat the thermal equilibrium buildup and may sample more than one temperature reading.

After S/C #2 19 returns a valid temperature measurement to the microprocessor 9 via the I/O bus 15, the microprocessor 9 through the same bus turns the recording indicator 31 off and so the user knows that it is now permissible to remove the temperature probe from the functional position. The logic for the preceding procedure is shown is Section B along the path from SN=6.

At this point (Section B line b−SN=0 input?) the microprocessor 9 stores the temperature value measured in RAM 13 in the area described as TT. The user is now expected to enter information concerning the current status of various of her body parameters into the fertility computer through input device 29. As previously stated, the input device 29 consists of six momentary contact pushbutton switches. These switches, together with the various register groups, form a structure which enables ovulation to be predicted ahead of time based on the current status of various body parameters, accounts for various gynecological disorders, and allows filtering out of irrelevant temperature readings already arrived at. Switch SW3 (48) is called "Discrepancy" and is pressed once if there is a small discrepancy such as waking up late and twice, if there is a large discrepancy, such as waking up with a sore throat or a fever. S/C #1 (18) is designed to ignore a level three or higher discrepancy input entry (i.e., if the switch SW3 is pressed three or more times S/C #1 (18) considers it pressed only twice). If a discrepancy level of two is entered, then the current temperature reading TT is not used in the computations. This is an important part of the filtering mechanism. If a discrepancy level one is entered, this is noted together with the current temperature. (The logic for this SW3 switch is shown in Section B of FIG. 3 at line SN=3).

Switch SW4 (50) of input device 29 is the "mucus change" switch. It is pressed when the user senses a change in her cervical mucus consistency. S/C #1 (18) is adapted to consider a mucus change input level four or greater as a mucus change input level three (i.e., it serves the user no purpose to press SW4 more than three times. For this logic, see Section B of FIG. 3 line SN=4). Together with DM and VM of group 6, SW4 forms an important structure which allows accurate prediction of the time of ovulation. As mentioned above, if the user is unable to sense this change, then the consistency of the cervical mucus may be determined by using (optional) vaginal mucus probe 108 with the appropriate algorithms.

Switch SW5 (52) is the "period" switch. This switch SW5 is pressed whenever the user notes blood per vagina. Although it serves the obvious purpose of alerting the fertility computer to the commencement of a new menstrual cycle, along with the DC input of register group 6 and register group 5, it forms a structure which is capable of recognizing certain gynecological disorders such as too long or too short a menstrual cycle. (The logic for SW5 is shown in Section B FIG. 3 at path SN=5?).

Switch SW1 (44) is the "clear" switch and is pressed if the user made a mistake and wants to erase something entered or start over again. (See SN=1? FIG. 3 Section B and the logic on line d commencing with CI>0? for the logic function of clear switch SW1). Switch SW6 (54) is the "display" switch and in this case is pressed once the user has finished entering the necessary information concerning the current status of her body parameters. (See SN=6? FIG. 3 Section B).

Cycle Management

At this point, we are ready to discuss the "cycle management" logic at line "a" of Section C of the Flow Chart, labelled "Cycle Management", where the DW register of group 6 is incremented by one (or set to one if previously containing a value of seven). In this manner, the DW register is set at a value corresponding to the correct day of the week. Next, the DC register of group 6 is incremented by one so that it contains a value corresponding to the current day of the menstrual cycle. The structure of the DC register is such that it does not increment past a value of forty-one. The inputs entered above through input device 29 are placed by the microprocessor 9 into certain areas of RAM 13. If the mucus change level entered above is level one or greater, then the microprocessor 9 stores the level of the mucus change in register VM of group 6 and at the same time, stores the values of DC and DM of register group 6.

Cycle 40 Days Plus

We are now at the point in the Flow Chart labelled Section C (cycle 40 days plus?). This is where the system begins to account for gynecological disorders, in this case accounting for cycles longer than 40 days. The microprocessor 9 examines the contents of register DC of 6. If a value of forty-one is found in DC of 6, then this means something is wrong, i.e., the menstrual cycle is too long and thus the microprocessor 9 sets flag F1 of 5 and then checks the RAM 13 to see if a level one period value was entered "today". If so, then the microprocessor 9 checks to see if flag F6 of 5 is set. If this flag is not set, then the microprocessor 9 sets it. If flag F6 was found to be set, then this indicates that a period level one was also entered yesterday. This indicates that a new menstrual cycle has begun. Thus, it is necessary for the microprocessor 9 to follow the following routine:

i. Calculate a new average cycle length such that CL=0.95CL+(0.05) (41).
ii. Reset registers DM, VM and MT of 6 to zero.
iii. Set flag F4 of register group 5 but reset all the other flags of 5.
iv. Shift the contents of register group 3 one register to the right.
v. Place the value of zero into register C1 of group 3 since the just completed cycle was longer than average.
vi. Place the value of two into DC of group 6 since this is the second day of the new cycle.

New Cycle

Next, referring to Section C of the Flow Chart labelled (New Cycle) the logic adapted to determine if a new cycle is occurring is shown. The microprocessor 9 checks the DC register of 6 and the RAM area 13 to see if a new menstrual cycle is beginning. If the value of register DC of 6 is eight or less, then this entire step is skipped because it is likely that any period values of level one occurring during the first eight days of the menstrual cycle are representative of the ongoing period rather than indicating that a new menstrual cycle is beginning or that a spotting event has occurred. If a period level one was not entered today and yet flag F6 is set indicating that a period level one was entered yesterday then the microprocessor 9 checks via the F-bus 26 to make sure that the value of DC of 6 is not less than the value of CL of 6 minus two because if this is true, then it indicates that spotting has occurred and thus the microprocessor 9 sets flag F3 of 5. If the day of the cycle is close to the average cycle length, i.e., DC is not less than CL minus two then this occurrence of a period level one value one day and not the next, is more likely representative of an oncoming menstrual cycle rather than spotting. In either case, since a period level one was not entered on that day (today), the microprocessor 9 resets flag F6. On the other hand, if a period level one was entered that day (today), then the microprocessor 9 checks to see if flag F6 of 5 is set, i.e., if there was also a period level one entry the previous day (yesterday). If not, then flag F6 of 5 is set; but if flag F6 of 5 was already set then this indicates two days in a row of period level one entries, therefore indicating a new menstrual cycle. Thus, the following routine, as shown on the right-hand side of FIG. 3 Section C (New Cycle), is followed as shown in the Flow Chart commencing at DM=VM=MT=0 column 4:

i. Reset VM, DM and MT of 6 to zero.
ii. Shift the contents of register group 3 one register to the right.
iii. If flag F4 of 5 is set then reset it to zero since this indicates that there was a cycle error one cycle ago and a new menstrual cycle has since passed.
iv. If flags F1 or F2 or F3 of group 5 are set then set flag F4 of 5 now so that a record is kept of the fact that a cycle error occurred in the menstrual cycle which is now terminating
v. Reset all the flags of register group 5 but if flag F4 is set then allow it to remain set.
vi. If the value of DC of 6 is smaller than twenty then this indicates a short cycle, i.e., a possible gynecological disorder, therefore, set flag F4 of 5, place a seven in C1 of 3 since this is a very short cycle, compute a new average cycle length (CL) such that CL=0.95CL+(0.05) (20) and place a two in DC of 6 since today is the second day of the new menstrual cycle.

If the value of DC of 6 is greater than or equal to twenty, then the length of the cycle which is terminating is not considered to represent a cycle error, therefore, continue with this routine.

vii. Compute a new cycle average such that $CL \cong (0.90).CL + 0.10DC$.

viii. If the value of register CN of 6 is less than three then increment register CN. The CN register is used by the fertility computer to keep track of the first three cycles of use of the fertility computer and so forms part of the structure which allows the fertility computer to compensate for having a dearth of information stored about the user which is necessary for accurate prediction of the time of ovulation.

ix. If the length of the cycle which is terminating is seven days or more shorter than the average cycle length, i.e., CL minus DC is greater than seven, then the value of C1 is set at seven, otherwise the value of C1 is equal to CL minus DC (both registers of Group 6) unless the difference is a negative number, in which case C1 is set equal to zero, i.e., indicating a cycle length equal to or greater than the average cycle length.

x. Register DC of 6 is given a value of two since this is the second day of the new menstrual cycle.

Another way of looking at the logic of Section C (New Cycle) is that in this routine we want to determine if a new cycle has occurred. The first column of Section C checks to see if the day of the cycle is 8 or less. If so, then any spotting that would occur is due to the present period so the processor proceeds directly down column 1 of Section C to Section D "set Q1=1". On the other hand, if the day of the cycle is greater than 8 days, it's the 9th day or greater, the computer checks to see if a new cycle is occurring. The first thing checked is if PI is equal to 1. (See column 2) In other words, was one of the keys pressed corresponding to period "today". If it was not pressed, then the next thing checked is "Was the period value input switch pressed yesterday?" i.e., was F6 equal to 1. F6 is the flag which indicates the PI button was pressed yeaterday.

Next, in column 2, assuming PI was pressed yesterday, then F6 was set yesterday, and if that is true and there's no period today, the computer checks to see if the day of the cycle is smaller than the average cycle length minus 2. If this is true, F3 is set because it indicates spotting. On the other hand, if the user is pretty close to the expected day of the next cycle, in other words DC is not smaller than CL-2, where CL is the average cycle length, then it's not really spotting, it may indicate an oncoming period.

After this check is made, F6 (the flag indicating that a period happened yesterday) is reset because there was no period today; so F6 is equal to 0 and the processor proceeds to column 1 of Section D. On the other hand, referring to column 3, if there was a period today and if F6 was set indicating was there a period yesterday, we proceed to column 4. If F6 wasn't set, then we proceed down column 3 and set F6 equal to 1. In other words, the flag which indicates that a period happened today is set, so if this happens again tomorrow we know that there was a period yesterday also.

What the computer is doing in simple terms, is determining if there are two days in a row when the user is having a period. If there are two days in a row, then it means a new menstrual cycle has started which is what is indicated at the top of column 4. If the answer to "F6 equal to 1?" is "yes", then we proceed to column 4. It means there was a period today, there also was a period yesterday, thus a new menstrual cycle is beginning. If a new menstrual cycle is beginning, then there are a few things the microprocessor must set. The DM, VM and MT registers are cleared out, i.e., set to zero and the cycle number registers 3 are incremented by one.

Next, before using the value of CL, F4 is set to zero. The reason F4 is set to zero is it's a new month now. If there was any cycle error indicated the previous month, this clears it out. Next, the computer checks to see if there were any errors this month. In other words, is F1, F2 or F3 equal to 1? Or, was the period greater than 40 days (F1 is set) less than 20 days (F2 is set), or did spotting occur in the middle of a period (F3 is set). If that did happen, then F4 is set again (see Column 5), so that next month the computer knows an error occurred in the previous month.

Next, the other flags are cleared because a new menstrual cycle is commencing and the computer starts from fresh. Now, referring to column 4, the computer checks to see was this a menstrual period which was less than 20 days? Again, this is a procedure which provides for a mechanism to account for gynecological disorders. If the answer is "Yes, the cycle was less than 20 days", then we proceed to the right at column 6 and compute an average cycle length CL of 0.95 times the previous average cycle length CL plus $0.05 \times 20$; where 20 is the cycle length this month.

On the other hand, if this month, the cycle length was greater than 20, in other words it was a more normal cycle, the computation is as shown in column 4 wherein the weighting favors the present cycle length. For example, if the present cycle length is 27, then the average cycle length is computed as 90% of the previous cycle length plus 10% of DC wherein DC is 27.

Continuing in column 4 of the New Cycle C1 is then set. If the average cycle length minus DC is greater than 7 then C1 is set at 7. On the other hand, if everything was normal, if the condition is that DC is smaller than 20 is false, that is if the day of the cycle is greater than 20, it's a normal length cycle, a new cycle average is computed in column 4.

Next, the CN register is checked to see if CN is equal to 3 in order to keep track of what the cycle number is during the first few cycles of use of the fertility computer. The reason for this is that the computer is an artificial intelligence device. It learns on its own. Until about 3 months, the machine has not learned enough about the user to make very precise judgments. This is similar to a woman going to a gynecologist. She must come back a few times before the doctor can know enough about her to decide on her condition. The same thing occurs with the computer. Before the microprocessor can make an intelligent judgment, it has to accumulate sufficient information on the user. But, so that the machine can be used in the first three months of operation, a compensation factor is employed by keeping track of what the CN is. If a CN is smaller than 3, then when figuring fertility status, the computer errs on the side of safety. This means that there will be more days of the month that a woman may have to abstain if she wishes to avoid pregnancy.

The first month, there may be 10 or 12 days that she must abstain. However, by about 3 months, if the woman has fairly regular cycles, it should only be 4 to 6 days; which is very acceptable figure.

Next, the computer checks to see if the difference between the average cycle length and the current day is greater than 7, i.e., is it 1 week or more? If it is, then C1, the length of this month's cycle, is set to 7. On the other hand, if the day of the cycle is greater than CL, in other words it's a long cycle, then C1 is set to 0. Finally, if it's in the middle (DC is not greater than CL and CL-DC is not greater than 7) then C1 is set equal to CL, the length of the cycle, minus DC, the day of the cycle. In other words, if the average cycle length is 28 days and today's cycle was 26 days, then 28 minus 26 or 2 is stored in C1.

When all this is accomplished, we are now to the point where DC can be set to 2 since there have been two periods in a row that occasioned two PI's at level one. Since the day of the cycle begins on the first day there's blood, i.e., the first day a period occurs; therefore, today must be the second day by definition.

Fertility Status Routine

We have now reached Section D (F stat routine) of Flow Chart FIG. 3. It is at this point in the operation of the fertility computer that the cycle error status ER, pregnancy status PR, and of course, fertility status FS, of the user are computed. If the user were using the fertility computer simply to view her cycle error, pregnancy or fertility status, then the operation of the fertility computer essentially begins at this point. The symbol "x" on the diagram indicates that the direct mode of operation branches is here.

In the RAM 13 of FIG. 2 are three byte-long areas of contiguous memory which are labelled ER, PR and FS. These areas of RAM 13, i.e., ER, PR and FS hold values corresponding to the cycle error status, the pregnancy status and the fertility status, respectively. In the present embodiment, the various statuses can vary from a value of zero to two-hundred-and-fifty-five. If a particular status is zero, then its respective indicator, a simple LED, is in the "off" status. If a particular status is two-hundred-and-fifty-five, then the indicator LED (either 56, 58 or 60 of FIG. 1) is made to flash at its maximum rate of about four Hertz. At intermediate status values, the corresponding LED is made to flash at intermediate rates. The RAM 13 areas for storage of ER, PR and FS in the present embodiment, are one-byte long, therefore it is not possible to increment them past two-hundred-and-fifty-five; however, it is apparent that if desired, additional storage space can be provided.

The first thing the computer does is check to see if any of the flags F1–F3 have been set indicating possible errors. Through the F-bus 26, the microprocessor 9 checks to see if any of flags F1, F2, F3 or F4 of 5 are set. As indicated in Section D of the Flow Chart, column 1, if either of flags F1, F2 or F3 are set then the ER value of RAM 13 is incremented by two-hundred-and-twenty-three. If flag F4 is set; then the ER value of RAM 13 is incremented by one-hundred-and-twenty-seven (column 2). The purpose of this step is to increase the ER value of RAM 13, i.e., the cycle error status; if any of the flags of group registers 5 have been set indicating that a cycle error has occurred.

Next, the microprocessor 9 searches through register group 3 using an algorithm which finds the most recent cycle which had the shortest cycle length but was not seven or more days shorter than the average cycle length, i.e., the algorithm finds the smallest n where $C_n$ is largest but wherein $C_n$ does not contain a value of seven. (Note: The structure of register group 3 is such that the larger the contents of a certain register then the shorter the length of the cycle which it represents. It should also be understood that if the fertility computer is built from discrete logic circuits then the above step, as well as other steps described in this description, could be accomplished with logic gates forming a comparator circuit and without the need for an algorithm.) Once the desired cycle is found, the microprocessor 9 checks to see if it is within the last five cycles, i.e., $n = <5$, because if the shortest cycle occurred more than five months ago, it is permissible to find and use the next shortest menstrual cycle. The contents of the particular register chosen above is placed by the microprocessor 9 into the RAM 13 area called TV, meaning Temporary Variable. The TV represents the value of the user's shortest cycle length and is physically stored in RAM 13. It represents in essense the difference between the number of days of the shortest cycle length and the average cycle length. For example, the computer essentially scans through previous cycles and finds that four months ago the user had a cycle length which was only 24 days while her average cycle length is 27 days. Her shortest cycle was 3 days shorter than her average cycle length. In this case, a $TV = 3$ is put into RAM 13.

Computer Differential

Referring now to Section E of Flow Chart FIG. 3, the microprocessor 9 then checks register group 3 to see if any menstrual cycles recently occurring were really short, i.e., are the contents of C1 or C2 or C3, equal to seven. This and the previous step are important in accurately predicting the time of ovulation. If the user previously had short menstrual cycles then statistically there is good reason to believe that this may happen again. If the more rigid method of using a fixed, predetermined time interval from the beginning of the menstrual cycle in order to predict ovulation is used, then there is a good chance that on occasion the predicted time of ovulation will be after ovulation has already taken place, an event that could prove unfortunate to a woman using such a device for purposes of contraception. In contrast, the flexible statistical method of predicting time of ovulation used by the present invention, is combined with a method of predicting the time of ovulation based with a method of predicting the time of ovulation based on the current status of various body parameters to allow the most accurate prediction of the time of ovulation. Thus, if either of C1 or C2 or C3 are equal to seven, the microprocessor 9 increments the value of TV in RAM 13 such that if TV was previously less than four (see column 3) it is incremented by three, otherwise, it is incremented by two (see column 2). Next, the microprocessor 9 once again checks register group 3 to see if in the past there were any very short cycles, i.e., do any two of the registers of 3 corresponding to four or more cycles ago have values of seven stored in them. If they do, then the microprocessor 9 increments the TV of RAM 13 by two if the TV previously was less than four, otherwise by one. In explanation, the TV is incremented somewhat more when a very short cycle occurs more recently. Although there is a chance it may happen again, if a very short cycle or two occurred nine months ago, there is a smaller probability than if a very short cycle occurred only two months ago.

As previously mentioned, unless the register groups 3-6 of the fertility computer 40 are previously programmed, for example, via the expansion interface socket 30 and I/O bus 15, using an external device with the user's gynecological and other histories, then there must be a mechanism to compensate for the fertility computer's ignorance of its user's characteristics during the first few months of use. Thus, if the value of the CN register of 6 is one then TV of RAM 13 is incremented by two, if the CN is equal to two then the TV is incremented by one. Other similar sorts of compensation may be employed.

It should now become apparent that the more likely the user is to have a very short cycle or the larger the dearth of statistical information accumulated on the user then the larger the value of TV will be. With this in mind, the microprocessor 9 now computes what is called the "differential" as follows:

i—Fetch the value of CL from register 6.
ii—Subtract fourteen from the value of CL.
iii—Subtract from the above intermediate result the value of TV in RAM 13.
iv—Subtract three from the above intermediate result and place the new result in the area of RAM 13 labelled DF.
v—If the value of DF is less than five then place the value of five in the DF of RAM 13.

The "differential" DF is part of the mechanism which allows the fertility computer to predict the time of ovulation. Note that it is related to the average cycle length, i.e., the value stored in the CL register of 6. If the user has short cycles on the average, then the differential is smaller. This is important because the differential tells the fertility computer on what day of the current menstrual cycle to be alert for the reasonable probability of the earliest possibility of conception resulting from intercourse. Since ovulation is normally fourteen days before the next menstrual cycle, fourteen days are subtracted from the average cycle length to indicate on what day of the current cycle ovulation is statistically most likely. Since the medical literature indicates that even women with regular menstrual cycles may ovulate a day or two earlier than expected, and since sperm may survive two to three days in the female genital tract, a value of three is also subtracted from the cycle length to give the *earliest* day of the current cycle on which to expect conception if intercourse results. Furthermore, if the TV in RAM 13 is non-zero, then this too must be subtracted from the average cycle length, thus producing a smaller differential which indicates that conception resulting from intercourse may occur even earlier. For example, if the user has an average cycle length of twenty-eight days, and a value of one in TV of RAM 13, then her differential is 28-1-14-3, or ten. That is, statistically the fertility computer indicates that the user may conceive, if intercourse occurs, as early as after the tenth day of her current menstrual cycle. It is important to remember that this is a statistical prediction of the time of ovulation and that the fertility computer uses this result along with (i) the current status of dynamic body parameters, and (ii) the consistency of the cervical mucus in order to accurately predict when ovulation will occur and uses this prediction in the computation of fertility status. If a cycle error occurs, then the error status is incremented, as described above, and although not shown, it may be desirable to incorporate any cycle errors which have occurred into the TV of RAM 13 or directly into the differential such that the latter is reduced even further.

Update Temperature Base

We are now at Section F of the Flow Chart of FIG. 3, which has nine principal columns as shown. At this point, the microprocessor 9 must update the contents of register group 4, in other words, bring the basal body temperature measurements up-to-date. Of course, if the user is at the time simply using the fertility computer to check her fertility or other statuses, i.e., and she has not entered her basal body temperature and other relevant parameters, then this step is skipped entirely by the fertility computer. Internal flag Q1 enables the temperature update to be skipped. But assuming an up-date is being entered, the microprocessor 9 via the F-bus 26 checks to see if flag F7 of 5 is set. If it is set, then this means the rise in basal body temperature associated with ovulation and the subsequent drop which occurs if the ovum is not fertilized have already occurred, and thus, the routine of Section F can be skipped. Also (see column 3) if the value of register DC of 6 is two or less then it is too early to expect a rise in basal body temperature associated with ovulation and too unstable to compute a median temperature and so the routine of Section F step would be skipped. The microprocessor 9 then (See column 4) compares the value of register DC of 6 with the differential arrived at above, i.e., DF of RAM 13. If the current day of the cycle (DC of 6) is less than or equal to the differential (DF of 13) then it is quite unlikely that ovulation and hence a rise in basal body temperature has occurred at this time, because it is now near the end or after the user's period and thus, serum progesterone levels have dropped and consequently so has the basal body temperature. Thus, since at this time and continuing until one day after the differential, it is quite unlikely that the basal body temperature is elevated, an average (albeit weighted) basal body temperature is computed and stored in register MT of 6 (see column 9). If today's discrepancy level entry was a two, then as part of the filtering mechanism today's basal body temperature is not stored in register group 4 nor is it used in the computation of the average non-elevated basal body temperature, i.e., this whole step is skipped (see column 8). If the microprocessor 9 finds that the value of register TC of 6 is zero (see column 9) then this means that today is the first day that an average temperature is being computed, and so, to start the process off, the absolute value of the temperature measured today is retrieved from RAM 13 by the microprocessor 9 and placed in the MT register of 6. If the value of register TC of 6 is less than ten, then it is incremented by one. Now the average non-elevated basal body temperature is computed. In doing so, the filtering mechanism takes into account whether a discrepancy level one was entered by weighting today's temperature measurement less if the latter is true.

On the other hand, if the current day of the cycle is greater than the differential, i.e., the value of register DC of 6 is greater than DF of RAM 13 but the rise in basal body temperature associated with ovulation has not occured yet, i.e., flag F5 of 5 is not set, then today's temperature reading is simply filtered and stored in register group 4. The following routine is followed (column 5).

i. If the value of DC of 6 is equal to the value of DF of RAM 13 plus one, then set TC of 6 to zero. (TC is reset because the point in cycle has been reached where temperature values are stored in register group 4 and register TC of 6 is adapted to contain a value corresponding to how many valid temperature readings have been stored in register group 4 for this portion of the cycle.)

ii. If today's discrepancy level entered was equal to two then the remainder of this entire step is skipped because the temperature reading is unfit to be used.

iii. Shift the contents of register group 4 by one register to the right.

iv. If the value of register TC of 6 is less than ten, then increment register TC of 6 by one.

v. If the absolute value of today's temperature reading minus the value of register MT of 6 (the non-elevated averaged basal body temperature) is greater than a certain threshold value (which is specified in the program storage area 14 and is a function of the sensitivity setting input 33) then set the high order of the two bits stored in register T1 of 4.

vi. If a discrepancy level one input was entered today then set the low order bit of the two bits used in register T1 of 4.

If, on the other hand, flag F5 of register group 5 is set, then this indicates that the rise in basal body temperature associated with ovulation has occurred. However, since the microprocessor 9 determined above that flag F7 of 5 was not set, two things must be done by the fertility computer. First, during the three days following the rise in basal body temperature, this new elevated temperature must be measured each day for three days so that a new elevated basal body temperature average can be stored in register MT of 6. As above, this temperature average is weighted in favor of those days when a zero level discrepancy input is entered. Second, starting four days after the completion of the rise in basal body temperature, i.e., four days after flag F5 of 5 becomes set, the absolute value of the daily basal body temperature measured is compared with the value of register MT of 6. As before, if the measured temperature crosses threshold (i.e., the difference of the value of MT of 6 minus the absolute value of today's measured basal body temperature is greater than a certain threshold value which is specified in the program storage area 14 and is a function of the sensitivity setting input 33) then the high bit of the two bits used in register T1 of 4 is set. (NOTE: Register T1 of 4 is empty because, as above, the contents of register group 4 have been shifted by one register to the right with register TC of 6 keeping track of how many valid temperatures have been stored after flag F5 of 5 was set.) If a level one discrepancy input was entered today, then the low order bit of the two bits used in register T1 of 4 is set. It should be mentioned that as before, if a discrepancy level two input was entered today, then as part of the filtering mechanism the temperature reading is considered unfit and thus, the entire step is skipped.

Compute Fertility Status

Now that the temperature measurement register group 4 has been updated, the fertility computer can move on to the next step and compute the fertility status Section G. Although the day of the week was previously incremented, the new day of the week has not been displayed yet. Thus, the microprocessor 9 fetches the value of register DW of 6 through the F-bus 26 and sends this value through the I/O bus 15 to S/C #5 (21) which causes the LED corresponding to the appropriate day of the week to go on.

The fertility status is calculated mainly from the day of the cycle equal to the differential DF to the day of the cycle when flag F5 of 5 is set. Since flag F5 of 5 is not set until at least two days after ovulation, it is presumed that after this day, the ovum is no longer capable of being fertilized and thus the user's fertility status is zero. Before the day of the cycle (i.e., DC<DF) equal to the differential DF it is unlikely, based on statistical assumptions, that ovulation will occur. However, since on occasion, ovulation may occur quite early in a woman who normally has regular menstrual cycles, a structure exists in the present invention to correlate changes in the status of various dynamic body parameters with the user's fertility status. In the case of the prototype fertility computer being described, if before or on the day of the cycle equal to the differential the value of DM of 6 is greater than or equal to four, then the fertility status, i.e., FS of RAM 13 is incremented by a multiple of thirty-two where the number of multiples is given by the value of register VM of 6. (See column 3.) On the other hand, if the day of the cycle is such that it is greater than the value of the differential DF and if the basal body temperature rise is not complete yet, i.e., the value of DC of 6 is greater than the value of DF of RAM 13 and flag F5 of 5 is not set, (See column 1 Section G at DC>DF and F5=0?) then computation of the fertility status is somewhat more complicated.

In this sense, the computer represents a more realistic point of view. During this part of the cycle there is a degree of uncertainty, you could be fertile or you could not. And this is important, first for the couple that wants to have a child, so that during the day of peak fertility they should try to have intercourse many times for the best possible results, while perhaps, if the fertility light is blinking a little bit less, there is not sufficient reason to expend all that energy. Secondly, for someone using this device as a contraceptive, it is important also to know the relative degree of fertility. If, for example, the user is a single woman who doesn't want to get pregnant at all, and the light is on even a little bit, she should use another type of contraceptive and not take any chances if she wants to get to 99% reliability. But, if the user is married and doesn't desire children for a few more years, but not to the extent of abstaining ten days a month, she may choose to abstain only three or four days a month when the fertility status is at maximum.

The microprocessor 9 first checks register group 4 to see if there are at least two temperature measurements which have crossed threshold (See column 2). If two such temperature measurements are not found, then it appears that ovulation has not occurred yet so that the ovum is no longer viable and thus the user must be alerted to her fertile status. The fertility status, or FS or RAM 13, is thus incremented a certain amount based on the following factors: more so if a cycle error occurred last month, i.e., flag F4 of 5 is set (F4=0?), if the current day of the cycle is closer to the statistically expected time of ovulation (DC>CL-14-3), if a mucus change input was entered after the day of the differential, i.e., the value of register DM of 6 is greater than DF of RAM 13 (DM>DF?), the greater the level of the mucus change input, i.e., the value of register VM of 6 and the more recent the day the last mucus change input was entered, i.e., the greater the value of register DM of 6.

The above can be seen in the flow chart Section G at column 2 where the value of FS is initially determined by one of four equations depending on whether the day of the cycle is greater or less than CL-14-3 and whether F4=0 as follows:

---

Equation 1:

-continued

```
F4 = 0 ? = YES
DC > CL - 14 - 3 ?   NO
Then FS = FS + 16 · [DC - (DF + 1)]
Equation 2:
F4 = 0 ? = YES
DC > CL - 14 - 3 ?   YES
Then FS = FS + 32 · [DC - (DF + 1)]
Equation 3:
F4 = 0 ? = NO
DC > CL - 14 - 3 ? = NO
Then FS = FS + 32 · (DC - DF)
Equation 4:
F4 = 0 ? = NO
DC > Cl - 14 - 3 ? = YES
Then FS = FS + 64 · (DC - DF)
```

On the other hand, if the microprocessor 9 has found two temperature measurements which have crossed threshold it proceeds to column 3 and employs the algorithm shown to determine whether or not a temperature rise indicative of ovulation has occurred. This algorithm is the last component in the mechanism which filters the temperature measurements. Basically, it requires that in order for the conclusion that ovulation has occurred to be reached there must be three recent temperature measurements in a row which have crossed threshold or at least four recent elevated temperature measurements with perhaps a nonelevated measurement stuck in the middle. Additionally, the requirements of the algorithm become more rigid if the current day of the cycle is still several days before the statistically expected day of ovulation or if there are level one discrepancy inputs alongside the various temperature measurements. If the fertility computer determines that a basal body temperature rise indicative of ovulation has occurred then (See column 5 or 3a or 3b) flag F5 of 5 is set, register TC of 6 is reset to zero, and since ovulation occurred at least two days ago the fertility status, or FS of RAM 13, is kept at zero. If the fertility computer does not think that ovulation has occurred for certain, then the fertility status will be computed as before, but it will be somewhat less depending on the probability that ovulation might have already occurred two days ago, which would be based on the number of elevated temperature measurements, when they occurred and how many discrepancy level one inputs are associated with them.

Compute PR Status

If flag F5 of 5 is set indicating that ovulation has taken place but flag F7 of 5 is not set indicating that basal body temperature has not returned to baseline yet, then the fertility computer must determine the user's pregnancy status, as shown in Section H of the Flow Chart. If the ovum is fertilized successfully, then the serum progesterone level remains elevated and so does the basal body temperature. If the value of register TC of 6 is not greater than five (TC>5?), i.e., if at least six days have not passed since it was determined that the basal body temperature was elevated indicating that ovulation had occurred two days before, then an insufficient number of temperature readings have been stored in register group 4 and so this step is skipped entirely today. If there are a sufficient number of temperature readings stored in register group 4 then the microprocessor 9 checks the latter to see if there are three recent depressed temperature measurements or four recent depressed measurements with an elevated one in the middle. As above, if more temperature measurements are encountered which correspond to a discrepancy level one input then the fertility computer is less likely to indicate that the criteria for return to baseline basal body temperature have been met. If the fertility computer determines that a return to baseline basal body temperature has occurred, then flag F7 of 5 is set and the pregnancy status, or PR of RAM 13 is kept at zero since the return to baseline basal body temperature indicates that successful fertilization of the ovum did not take place. On the other hand, if the current day of the cycle exceeds the average cycle length by two days (DC>CL+1) and a return to baseline basal body temperature has still not occurred, then it is possible that successful fertilization did take place. In this case, the pregnancy status, i.e., PR of RAM 13 is incremented in multiples of twenty where the number of multiples is given by the number of days the current day of the cycle, i.e., the value of register DC of 6, exceeds the average cycle length, i.e., the value of register CL of 6.

Next Period and Display

The fertility computer now determines, as shown in Section I of FIG. 3, if the user is expected to have period within one week of the current day of the cycle, i.e., if the value of register DC of 6 is within seven days of the value of register CL of 6. If so, then the day of the week of the commencement of the expected period is equal to the value of register CL of 6 minus the value of register DC of 6 plus the value of register DW of 6. If a negative result or a result greater than seven is obtained, then the microprocessor 9 adds seven or subtracts seven to the previous result to give the day of the week the next period is to begin on. The microprocessor 9 then instructs S/C #5 (21) via the I/O bus 15 to indicate on indicator 28 that this day of the week is the expected commencement of the next period, in which case, an LED corresponding to the particular day of the week begins to flash.

The microprocessor 9 now accesses to the RAM 13 via the data/address bus 12 and fetches the values of ER, PR and FS in RAM 13. The microprocessor 9 then transmits these values, via the I/O bus 15, to S/C #7 (25), S/C #8 (24) and S/C #9 (23), respectively and the error status, pregnancy status and fertility status are respectively indicated on indicators 36, 35 and 34. As mentioned before, indicators 36, 35 and 34 consist of one red LED each. If the particular status value is zero then the particular LED is turned off. If the particular status value is maximum then the particular LED flashes at the maximum rate of about four Hertz. If the particular status value is intermediate then the particular LED flashes at an intermediate rate.

In order to extend battery 2 life if the user does not turn off the On/Off switch 1, then the microprocessor 9 will automatically do so after a certain time interval, as determined by the program storage area 14 and the programmable timer 11.

Table 1 below lists readily available sources for parts to manufacture the fertility computer herein described.

TABLE 1

The item numbers refer to the block diagram, FIG. 2.
A number in parentheses indicates how many of the part
are required. Note the following abbreviations:
TI = Texas Instruments, YSI = Yellow Springs Instruments,
A-B = Allen-Bradley.

| Item | Description | Manufacturer | Part |
|---|---|---|---|
| 1 | On/Off Switch, SPST | Alcoswitch | SLSA-120 |
| 2 | Battery, 4 C cells | Eveready (4) | E93 |
| 3 | Non-volatile memory register | Fairchild | F4731 |
| 4 | Non-volatile memory register | " | " |
| 5 | Non-volatile memory register | " | " |
| 6 | Non-volatile memory register | " | " |
| 7 | Self-test circuit (2 parts) | Motorola | 1N4730 |
|   |                             | Motorola | LM 339 |
| 8 | Self-test indicator (LED) | TI | TIL224 |
| 9 | Microprocessor | Intel | 8080 |
| 10 | Oscillator | " | 8224 |
| 11 | Timer | " | 8253 |
| 12 | Interconnection wiring | " | |
| 13 | RAM | Signetics | 82S09 |
| 14 | ROM | Intel | 2716 |
| 15 | Interconnection wiring | | |
| 30 | Expansion interface socket | TRW | DEC-9S |
| 17 | Signal conditioning #4 | TI | SN75451B |
| 18 | S/C #1 | TI | SN7414 |
| 19 | S/C #2 | National | ADC0808 |
| 20 | S/C #3 | " | " |
| 21 | S/C #5 | TI | SN75497 |
| 22 | S/C #6 | " | " |
| 23 | S/C #9 | " | " |
| 24 | S/C #8 | " | " |
| 25 | S/C #7 | " | " |
| 26 | Interconnection wiring | | |
| 27 | S/C #10 | National | ADC0808 |
| 28 | Day-of-week LED display | TI (7) | TIL224 |
| 29 | Keyboard switches | Alcoswitch (6) | MSP-103C |
| 108 | Mucus probe, as described in body of application | | |
| 31 | Recording indicator LED | TI | TIL234 |
| 32 | Temperature probe | YSI | 44106 |
| 33 | Sensitivity setting potentiometer | A-B | RP103U |
| 34 | Fertility status LED | TI | TIL228 |
| 35 | Pregnancy status LED | " | " |
| 36 | Cycle error status LED | " | " |

Equivalents

In describing the present embodiment, very little attempt has been made to discuss possible variations. Alternate aspects of the present invention are now presented in a more comprehensive manner.

Since the fertility computer can interface with a digital general-purpose computer it could be used to form the structure of the following devices or be used in coordination with the following devices and/or in the embodiment of the following devices or any combination of them: alarm clocks, wristwatches, timepieces, articles of clothing, calculators, biorhythm computers, horoscope computers, eyeglasses, or in embodiments suitable for use with animals. If combined with a radio, for example, the radio could play a tune while a temperature measurement is being taken. Or if combined with an alarm clock, the latter could remind the user not to miss a temperature reading.

It should be mentioned that the same factors which determine fertility status i.e., mucus change and BBT change, also determine ovulation status. Accordingly, it is contemplated that the apparatus herein may be equally employed to determine whether ovulation has occurred.

The possible input and output devices, whether built into the fertility computer or attached through the expansion interface socket, include the following and any combinations thereof: a stand-alone device which can access or change the internal registers, a device to allow any general purpose computer to access or change the internal registers, multi-colored LED's or other point-viewed light sources or devices changing the intensity or color of light viewed such as LCDs, alphanumeric displays, alphanumeric or graphics printers, chart recorders, aural indicators, such as voice circuits, tones and alarms, additional indicators indicating the status of whatever internal register desired, tactile indicators, temperature probes for use in any body cavity or for use by skin contact or for use in body folds, input switches of a mechanical or electrostatic or resistance change or capacitators or magnetic nature being sealed or not, ultrasonic probes, probes which help detect ovulation by changes in the body's bioelectrical potentials, probes which help detect ovulation by changes in the vaginal and/or cervical fluid and mucus physical properties, probes which help detect ovulation by change in biochemical properties (for example, an increase in glucose concentration of the cervical mucus), timing devices, calculator keypads, computer terminal keyboards, or speech-recognition input.

The basic structure of the fertility computer shown in FIG. 2 may be enhanced by providing more registers and additional RAM along with the appropriate algorithms to enable it to do the following or any combination thereof: use by more than one user, storage of the actual or coded temperature measurements for extended periods of time, diagnostic gynecological computer, storage of the actual or coded cycle lengths for extended periods of time, redundant flag and miscellaneous resisters, redundancy of all registers, redundancy of battery, redundancy of all parts, user aid (i.e., instructing the user how to use the device).

The preferred embodiment of the present invention described above should prove to yield the most accurate results concerning the user's fertility status. However, for reasons of simplification and resultant economy, the fertility computer described above may be stripped of some of its features, although still retaining the spirit of the present invention. For example, consider the alternate embodiment of the fertility computer presented below.

Figure 5:
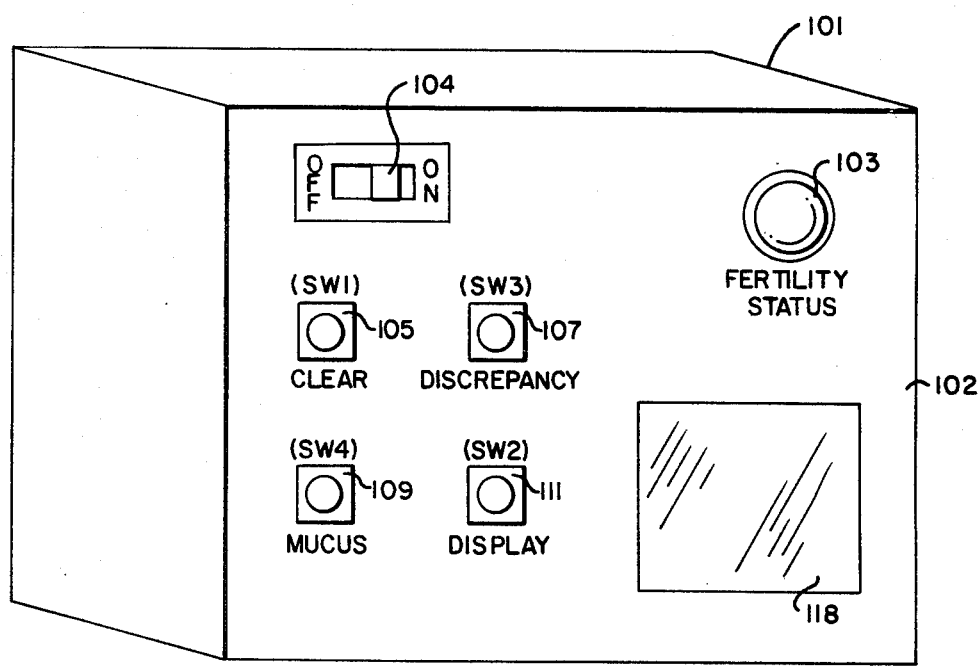
FIG. 5 is a perspective view showing the exterior configuration of an alternate embodiment of the invention.

FIG. 5 depicts an arrangement of the components of the alternate embodiment of the invention comprising a simplified version of the fertility computer 101. An LED 103, preferably red in color, is "on" if the user's fertility status, as computed by the fertility computer, is in the significant range; it is "off" if the fertility status is deemed to be insignificant by the computer. Switch 104 is used to turn the unit "on" or "off". Switches 105, 107, 109 and 111 allow the user to enter information to the fertility computer. Instructions on how to use the device are displayed in a prominent location 118.

Figure 6:
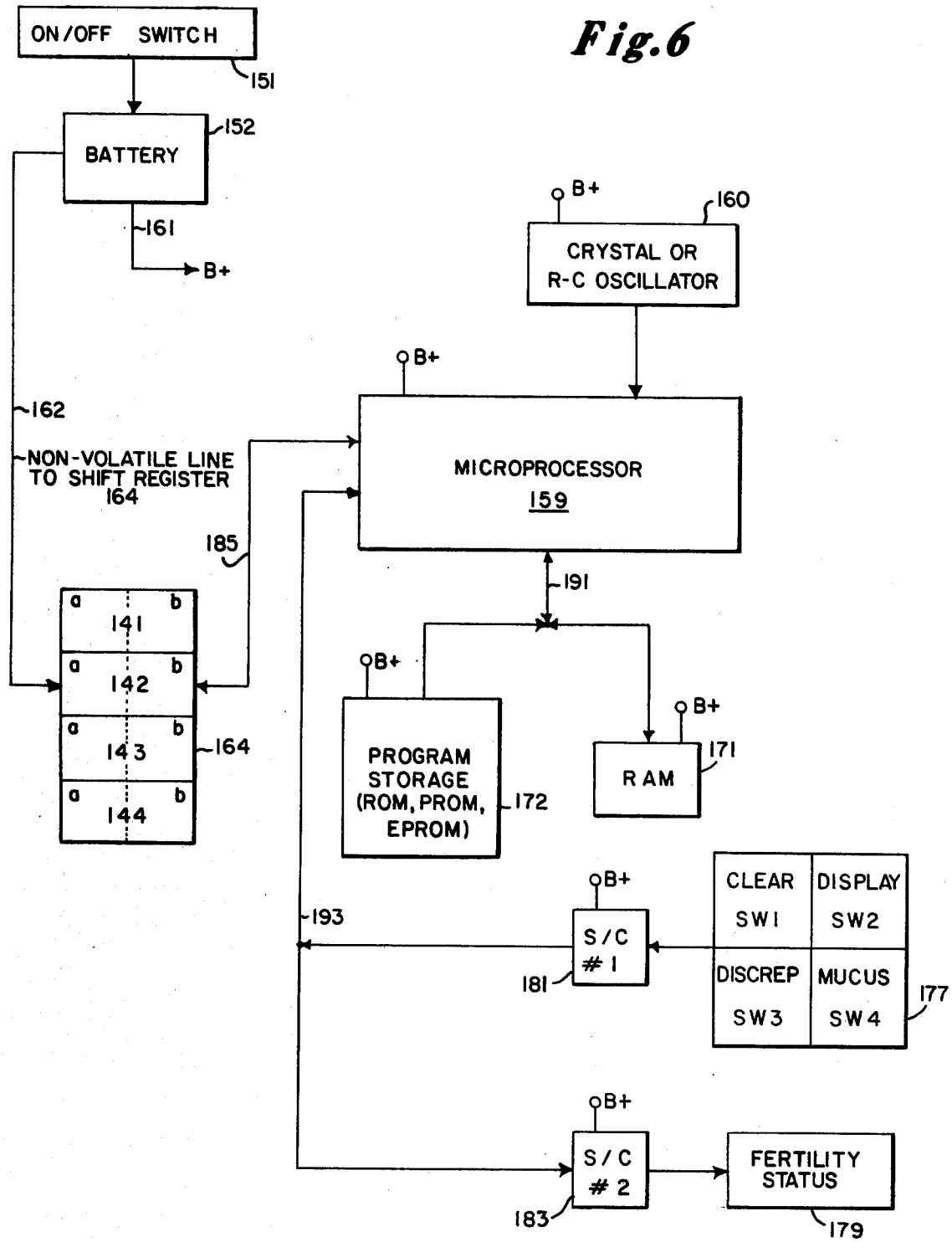
FIG. 6 is a block-diagram of the embodiment of FIG. 5.

FIG. 6 is a block diagram of an economy version of the fertility computer. The battery voltage is constantly applied to shift register 164 via buss line 162 so that the contents of register 164 remain non-volatile. The voltage from battery 152 is applied to the remainder of the circuit via buss line 161 and is volatile in that "on/off" switch 151 may connect or disconnect the battery 152 to buss line 161.

A microprocessor 159 is used as the controlling element in this circuit, although as mentioned previously, discrete logic circuits could be substituted to do the same function. A data bus 191 connects the microprocessor 159 to working read/write RAM memory 171 and read-only program storage memory 172. An input/output buss 193 connects the microprocessor 159 to input switches 177 and output indicator 179. Signal conditioner #1 (181) receives inputs from the keypad 177 and outputs them onto the I/O buss 193. Signal conditioner #2 (183) receives an input from I/O buss 193 and outputs it to the fertility status indicator 179 which is a red LED.

The microprocessor 159 is connected to the 8-bit shift register 164 via the F-buss 185. The 8-bit shift register 164 is divided into four groups of 2-bit values, called M1, M2, M3 and M4. M1 141 corresponds to the data entered most recently while the contents of M4 144 would correspond to data entered four days ago, for example. Register group 164 is shifted by two bits to the right each day. If the "mucus change" switch, SW4 of 177 is pressed, then the high order bit of the appropriate two-bit register is set. If the "discrepancy" switch, SW3 of 177 is pressed, then the low order bit of the appropriate two-bit register is set. This is described in further detail below in connection with the logic charts.

Table 2 below lists typical components available for constructing the circuit depicted in FIG. 6.

TABLE 2

| Component Reference Number in FIG. 6 | Description | Supplier & Part Number |
|---|---|---|
| 151 | On/off SPST switch | Priority One Electronics, CAL-ST |
| 152 | Battery 4C cells | Eveready E93 |
| 159 | Microprocessor | Motorola #MC6808P |
| 160 | 1.00 MHz crystal | Priority One Electronics, #XTL 1.000 |
| 164 | 8-bit shift register (CMOS) | Motorola #4014-B |
| 171 | 1024 × 1 RAM | Motorola #2102AN-2 |
| 172 | 1024 × 8 EPROM | Motorola #2708 |
| 177 | Momentary-contact push-button switches | Jameco #K19 |
| 179 | Red LED | Priority One Electronics #LED |
| 181 | Line receiver | Motorola #MC1489P |
| 183 | Line driver | Motorola #MC1488P |

Sample components which are both inexpensive and readily available are listed in Table 2.

Figure 7A:
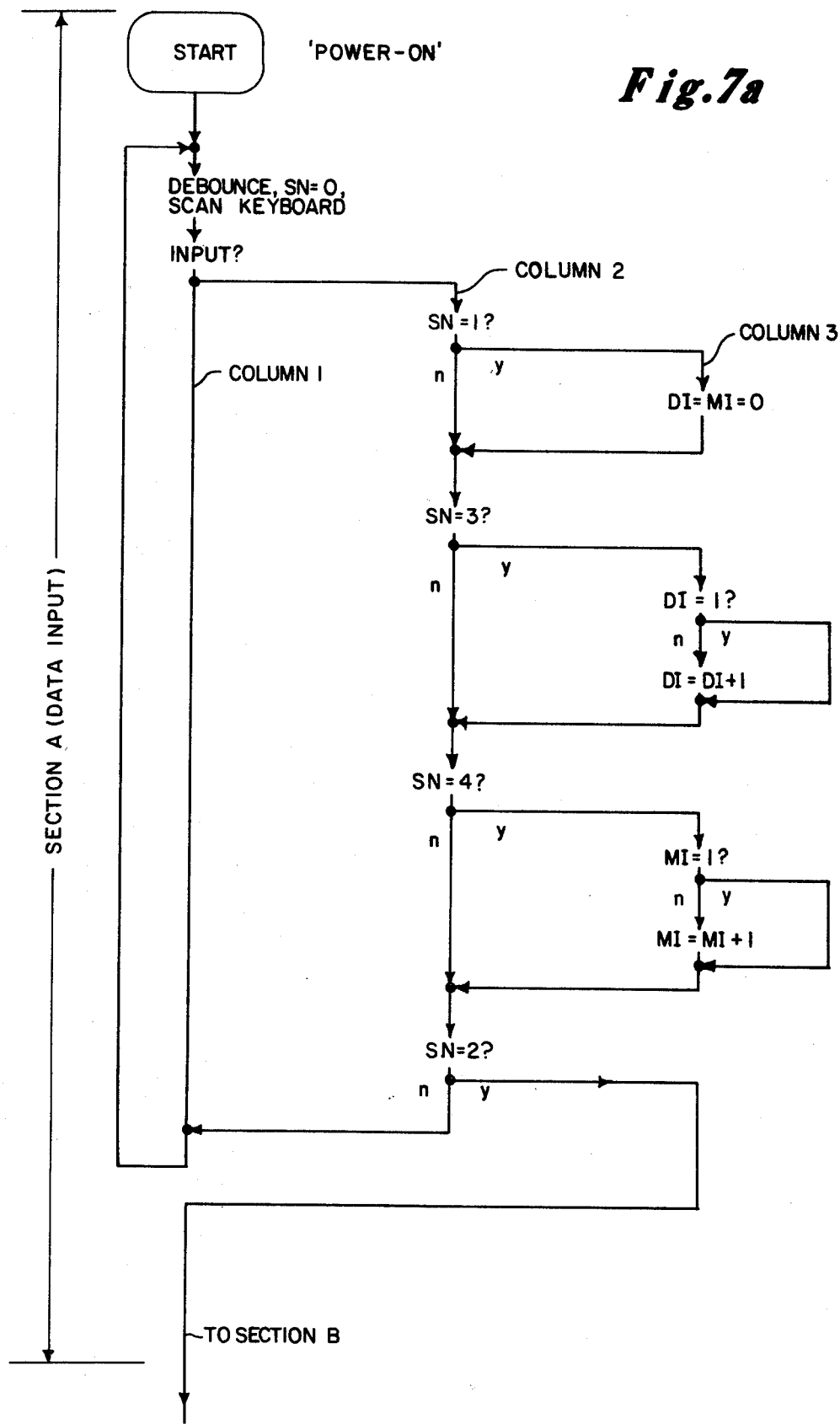
FIGS. 7a–7c is a flow chart showing the logic steps associated with the alternate embodiment of FIGS. 5 and 6.
Figure 7B:
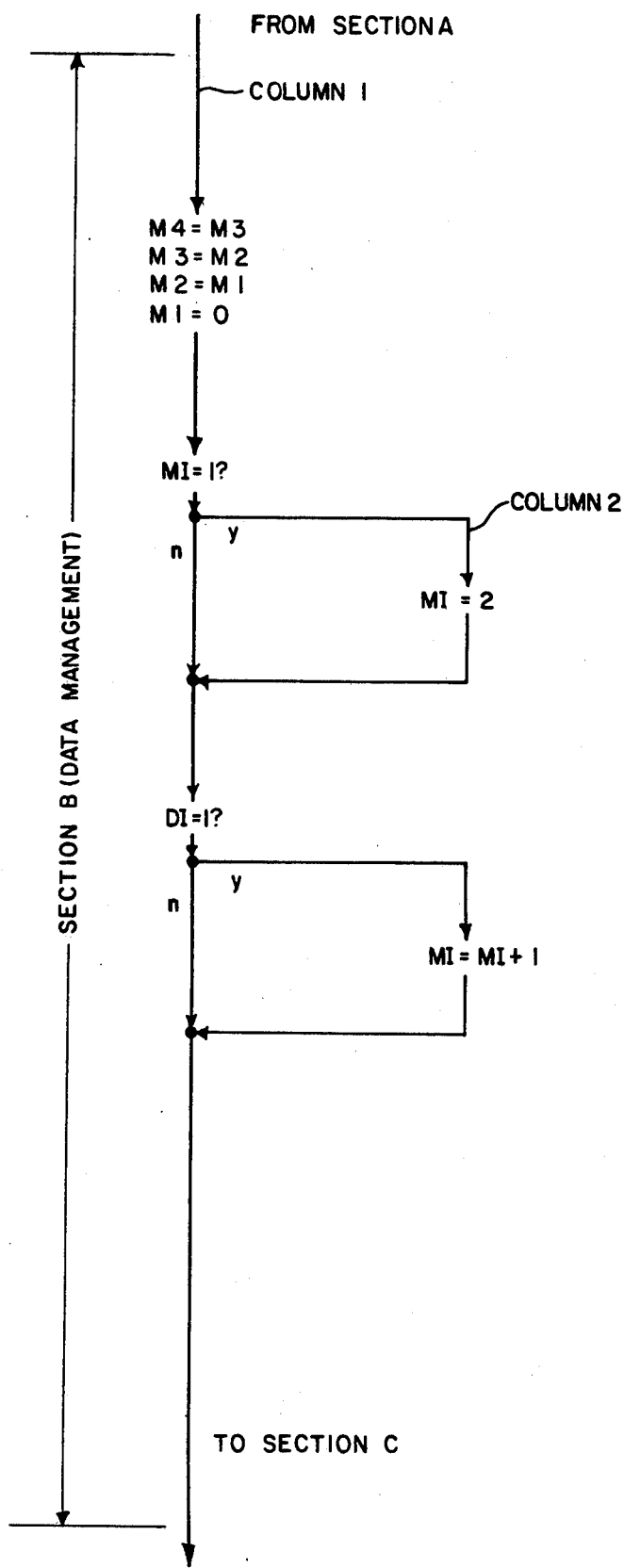
Figure 7C:
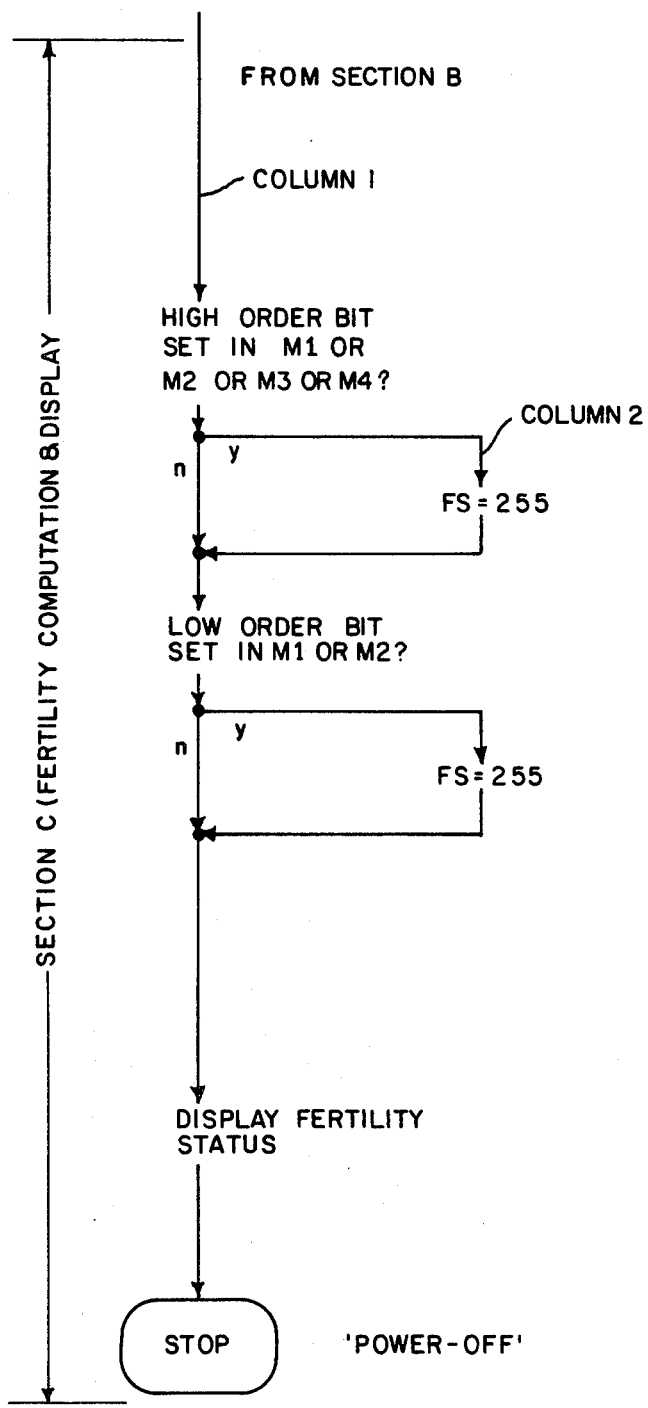

FIGS. 7a-c depicts the logic utilized in the economy fertility computer of FIGS. 5 and 6. Section A is used to allow the user to enter information on the status of one of her dynamic body parameters, in this case the quality and quantity of her cervical (or in some cases, oral) mucus. As previously mentioned, during most of the menstrual cycle, the cervical mucus is considered dry or tacky, but as ovulation approaches, there is a change in the quality of the mucus to a wetter, more elastic consistency, and often an increase in quantity also results. When the user experiences this "change in mucus" switch SW4 of 177 (FIG. 6) is pressed, and hence, the condition SN=4 in column 2 is true and thus MI in shift register 164 is set to one, as indicated in column 3. Similarly, if a user is not exactly sure of her cervical mucus status due to an on-going period, vaginal infection, intercourse the previous night, etc., then the discrepancy switch SW3 of 177 is pressed, and hence condition SN=3 in column 2 is true and thus DI is set to one, as shown in column 3. If the user makes an error in entering information, e.g. she hits the wrong key, then the clear switch SW1 of 177 is pressed, and hence the condition SN=1 in column 2 is true and thus DI and MI are reset to zero, as shown in column 3. When the user finishes entering the appropriate information she presses the display switch SW2 of 177, and hence, the condition SN=2 is true and thus, as shown in FIG. 7a, the logic progresses to section B on FIG. 7b.

The function of section B is to store the information entered in storage register 164. First, the register group 164 is shifted two bits to the right, such that M4=M3, M3=M2, M2=M1 and M1 is cleared. Then the high order bit of M1 is set if MI is equal to one, and the low order bit of M1 is set if DI is equal to one. The logic then progresses to section C on FIG. 7c.

The fertility status of the user is computed in accordance with the logic of FIG. 7c Section C. If there has been a change in mucus noted over the last four days, i.e., if the high order bit is set in either M1 or M2 or M3 or M4, then the fertility status, FS, is set to 255, as shown in column 2. If there has been a discrepancy noted over the last two days, i.e., if the low order bit is set in either M1 or M2, then the fertility status, FS, is set to 255, as shown in column 2. If the fertility status, FS, is zero then the fertility status indicator 179 remains off, but if it is equal to 255, then it is turned on.

In this manner above-described, a simple, relatively inexpensive device is provided wherein fertility status is computed taking into account information with respect to: (1) the status of a user's body parameters indicating the onset of ovulation, i.e., mucus change and (2) certain discrepancy factors which might indicate unreliability of measurements in (1) above. This information is stored in memory and the information in (1) is weighted in accordance with (2) and then used to predict fertility status.

Those skilled in the art will be able to ascertain, using no more than routine experimentation, other equivalents for the method and apparatus above described. Such equivalents are intended to be included within the scope of the following claims.

I claim:
1. A fertility computer comprising:
(a) storage means for storing data indicating:
(i) the day of the week, DW;
(ii) the day of a menstrual cycle, DC;
(iii) a user's average cycle length, CL;
(iv) the day of a menstrual cycle in which mucus change occurred, DM;
(v) the relative value of the change in (iv);
(vi) a plurality of the most recent Basal Body Temperature (BBT) readings of the user T(1)-T(N);
(vii) the number of menstrual cycles in which the computer has been used by the user, CN; and
(viii) a plurality of discrepancy indicators F1-F(n);
(b) data processing means for utilizing the above data to provide an indication to the user of current fertility status;
(c) switch means operable by a user for inputting data with respect to a user's menstrual cycle parameters, basal body temperature, and physical disturbances into said data processing means;
(d) a temperature sensor for producing an analog temperature signal indicative of the user's basal body temperature;
(e) converter means for converting said analog signal to a digital signal; and

(f) display means for displaying to the user whether of not the temperature sensor is in a functional position and when it is permissible to remove the sensor from the functional position.

2. The apparatus of claim 1 wherein the fertility status is computed by ascribing different values to such data depending upon:
(a) the liklihood of a discrepancy, or
(b) the user's average cycle length, or
(c) the relative value of the mucus change.

3. The apparatus of claim 2 wherein the discrepancy indicators are one or more of the following:
(a) a cycle of more than 40 days or less than 20 days;
(b) spotting within a cycle.

4. The apparatus of claim 3 wherein a factor in the computation is whether or not a BBT rise or drop has been completed.

5. A self-contained system for measuring and analyzing data which is indicative of a user's fertility and pregnancy status, comprising:
(a) a housing;
(b) an electrical power source inside said housing;
(c) switches mounted on said housing including a first switch to be pressed when the user senses blood per vagina indicative of a new period, a second switch to be pressed when a dry to wet change in the cervical mucus is sensed by the user, a third switch to be pressed when a disturbance in physical condition such as feeling ill is sensed by the user, and a fourth switch to be pressed when the user makes a mistake pressing one of the above switches and wishes to correct this mistake;
(d) a temperature sensor coupled to the housing comprising a thermistor which need not measure temperature accurately but only in a repeatable fashion;
(e) display means indicating
(i) correct operation of the system and
(ii) suitable power or
(iii) problems with either,
(iv) that the temperature sensor is still to be kept in a functional position within the mouth,
(v) the probability that the user is in the fertile phase of her menstrual cycle, and
(vi) the probability that the user is pregnant;
(f) a permanent memory consisting of a low power random-access-memory (RAM) device to which electric power is constantly applied and which is used to store among other data the current day of the menstrual cycle, lengths of a certain number of previous menstrual cycles if they exist, and values related in a predictable fashion to a number of previous or current temperature readings;
(g) a microprocessor coupled to an oscillator circuit, a read-only-memory (ROM), and said random-access-menmory (RAM) and input-output signal conditioners where said microprocessor interacts with the various elements it is attached to in accordance with a controlling algorithm preprogrammed in the ROM;
(h) self-test circuitry and logic means to determine whether circuit elements, including the electric power source and random-access-memory, are functional and convey this information to the user via said display means; and,
(i) temperature measurement and logic means to convert measured temperature of the temperature sensor to a digital signal related to the observed temperature and indicate to the user to keep the temperature probe in a functional position and to provide a signal to said display means until a certain period of time and/or certain thermal equilibrium is achieved.

6. The system of claim 5 including logic means for giving lesser or zero value to the digital signal representative of observed temperature if said third switch is pressed.

7. The system of claim 5 including logic means to disregard input from the first switch at the initial portion of the menstrual cycle.

8. The system of claim 5 including logic means to indicate that a new period is starting if the first switch has been pressed on at least two consecutive days.

9. The system of claim 5 including logic means to avoid obtaining and/or storing temperature measurements during the initial part of the menstrual cycle.

10. The system of claim 5 including:
logic means to allow computation from the stored cyclic information of a differential value which indicates the beginning of the fertile phase of the menstrual cycle and where said differential value is made smaller by previous menstrual cycles of short duration and by determination that the stored information is indicative of a relatively new unit and where said differential value is not used to determine the start of the fertile phase if the second switch is pressed during an appropriate time of the menstrual cycle but at a day of the current cycle smaller than the said differential value.

11. The system of claim 5 including logic means to disregard input from the second switch at the initial portion of the menstrual cycle.

12. The system of claim 5 including logic means to interpret stored temperature measurements to determine fertility status and ovulation wherein a user's temperature measurements taken on days of cycle smaller than the differential value are used to construct a representative baseline temperature and at days of a cycle equal to or greater than the differential value, a day's temperature measurement is interpreted as elevated if it exceeds the representative baseline temperature by a preset threshold value which value is in turn determined by a sensitivity value, and wherein a certain number of days after ovulation determination has been completed the day's temperature measurement is interpreted as depressed if the temperature measurement is exceeded by a representative baseline temperature value constructed from temperature measurements immediately following ovulation by a preset threshold value which is in turn determined by said sensitivity value, and wherein ovulation is determined to have occurred if three recent temperature measurements are interpreted to have been elevated where said elevated temperature measurements occur consecutively or within a duration of four or five days and wherein a certain number of measurements are associated with no disturbances and a certain number are associated with disturbances and a minority are not interpreted as elevated, and wherein the indication of no fertility or infertility is given to the user after ovulation determination is complete, where an indication of pregnancy is given to the user if the day of cycle is greater than the expected menstrual cycle length and several recent temperature values are not interpreted as depressed in a consecutive fashion.

13. An electronic apparatus for measuring and analyzing data which is indicative of a user's fertility and pregnancy status according to claim 5 further comprising means for determining and indicating the start of the next menstrual cycle.

14. An electronic apparatus for measuring and analyzing data which is indicative of a user's fertility and pregnancy status according to claim 5 further comprising logic means to indicate low and maximum probability of fertility and/or pregnancy.

* * * * *